(12) United States Patent
Fritzinger

(10) Patent No.: US 12,076,025 B2
(45) Date of Patent: Sep. 3, 2024

(54) POLYMER CUTTING BLOCK

(71) Applicant: DEPUY SYNTHES PRODUCTS, INC., Raynham, MA (US)

(72) Inventor: Daniel D. Fritzinger, Warsaw, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 295 days.

(21) Appl. No.: 17/741,898

(22) Filed: May 11, 2022

(65) Prior Publication Data

US 2023/0363768 A1 Nov. 16, 2023

(51) Int. Cl.
*A61B 17/15* (2006.01)
*A61B 17/00* (2006.01)

(52) U.S. Cl.
CPC .. *A61B 17/155* (2013.01); *A61B 2017/00477* (2013.01)

(58) Field of Classification Search
CPC .................................................. A61B 17/155
See application file for complete search history.

(56) References Cited

U.S. PATENT DOCUMENTS

| | | | |
|---|---|---|---|
| 2,181,746 A | 11/1939 | Siebrandt et al. | |
| 3,835,849 A | 9/1974 | McGuire et al. | |
| 4,191,861 A | 3/1980 | Walker | |
| D260,927 S | 9/1981 | Glenn | |
| D281,622 S | 12/1985 | Diamond | |
| 4,565,192 A | 1/1986 | Shapiro et al. | |
| 4,633,862 A | 1/1987 | Petersen | |
| 4,692,073 A | 9/1987 | Martindell et al. | |
| 4,718,413 A | 1/1988 | Johnson | |
| 5,002,547 A | 3/1991 | Poggie et al. | |
| 5,021,055 A | 6/1991 | Burkinshaw et al. | |
| 5,108,401 A | 4/1992 | Insall et al. | |
| 5,116,338 A | 5/1992 | Poggie et al. | |
| 5,129,907 A | 7/1992 | Heldreth et al. | |
| 5,129,908 A | 7/1992 | Petersen et al. | |
| 5,129,909 A | 7/1992 | Sutherland | |
| 5,147,365 A | 9/1992 | Whitlock et al. | |
| 5,174,693 A | 12/1992 | Lee et al. | |
| 5,178,621 A | 1/1993 | Cook et al. | |
| 5,222,955 A | 6/1993 | Mikhail et al. | |

(Continued)

FOREIGN PATENT DOCUMENTS

CN 101259044 A 9/2008
CN 101484085 A 7/2009

(Continued)

OTHER PUBLICATIONS

European Search Report for European Application No. 14157968.0-1654, dated May 15, 2014, 4 pages.

(Continued)

*Primary Examiner* — Sameh R Boles

(74) *Attorney, Agent, or Firm* — Barnes & Thornburg LLP

(57) ABSTRACT

An orthopaedic surgical instrument includes an all-polymer 4-in-1 cutting block having a number of polymer cutting guides. In some embodiments, the all-polymer cutting block is be embodied as a multi-piece cutting block, while in other embodiments the all-polymer cutting block is embodied as a single, monolith cutting block. Several methods for fabricating the different all-polymer 4-in-1 cutting blocks are also disclosed.

15 Claims, 29 Drawing Sheets

(56) References Cited

U.S. PATENT DOCUMENTS

| | | | |
|---|---|---|---|
| 5,250,050 A | 10/1993 | Poggie et al. |
| 5,258,032 A | 11/1993 | Bertin et al. |
| 5,284,482 A | 2/1994 | Mikhail et al. |
| 5,284,485 A | 2/1994 | Kammerer et al. |
| 5,312,409 A | 5/1994 | McLaughlin et al. |
| 5,382,254 A | 1/1995 | McGarry et al. |
| 5,403,321 A | 4/1995 | DiMarco |
| 5,415,663 A | 5/1995 | Luckman et al. |
| 5,470,328 A | 11/1995 | Furnish et al. |
| 5,484,451 A | 1/1996 | Akopov et al. |
| D367,531 S | 2/1996 | Price et al. |
| 5,499,984 A | 3/1996 | Steiner |
| 5,520,692 A | 5/1996 | Ferrante et al. |
| 5,536,271 A | 7/1996 | Daly et al. |
| 5,542,947 A | 8/1996 | Treacy |
| D373,635 S | 9/1996 | Price et al. |
| 5,575,793 A | 11/1996 | Carls et al. |
| 5,582,615 A | 12/1996 | Foshee et al. |
| 5,593,450 A | 1/1997 | Scott et al. |
| 5,611,802 A | 3/1997 | Samuelson et al. |
| 5,626,607 A | 5/1997 | Malecki et al. |
| 5,667,512 A | 9/1997 | Johnson |
| 5,683,397 A | 11/1997 | Vendrely et al. |
| 5,683,398 A | 11/1997 | Carls |
| 5,716,360 A | 2/1998 | Baldwin et al. |
| 5,716,361 A | 2/1998 | Masini |
| 5,716,362 A | 2/1998 | Treacy |
| 5,827,279 A | 10/1998 | Hughett et al. |
| 5,941,884 A | 8/1999 | Corvelli et al. |
| 5,944,723 A | 8/1999 | Colleran et al. |
| 5,957,926 A | 9/1999 | Masini et al. |
| 5,968,051 A | 10/1999 | Luckman et al. |
| 6,007,537 A | 12/1999 | Burkinshaw |
| 6,010,509 A | 1/2000 | Delgado et al. |
| 6,056,754 A | 5/2000 | Haines et al. |
| 6,074,425 A | 6/2000 | Pappas |
| 6,080,162 A | 6/2000 | Dye et al. |
| 6,190,391 B1 | 2/2001 | Stubbs |
| 6,205,884 B1 | 3/2001 | Foley et al. |
| D459,474 S | 6/2002 | Bratt et al. |
| 6,419,675 B1 | 7/2002 | Gallo, Sr. |
| D463,550 S | 9/2002 | Sherman |
| 6,551,316 B1 | 4/2003 | Rinner et al. |
| 6,589,248 B1 | 7/2003 | Hughes |
| 6,851,150 B2 | 2/2005 | Chiang |
| 6,854,919 B2 | 2/2005 | Neumann |
| 6,855,150 B1 | 2/2005 | Linehan |
| 6,866,667 B2 | 3/2005 | Wood et al. |
| 6,905,514 B2 | 6/2005 | Carignan et al. |
| D549,331 S | 8/2007 | Tomatsu et al. |
| 7,344,540 B2 | 3/2008 | Smucker et al. |
| 7,356,902 B2 | 4/2008 | Snider et al. |
| 7,566,335 B1 | 7/2009 | Scott et al. |
| 7,632,279 B2 | 12/2009 | Bastian |
| 7,780,594 B2 | 8/2010 | Hutton |
| 7,806,899 B2 | 10/2010 | Hogg et al. |
| 7,878,989 B2 | 2/2011 | McMinn |
| 7,891,071 B2 | 2/2011 | Collazo |
| D634,011 S | 3/2011 | Phillips et al. |
| D638,541 S | 5/2011 | Claypool |
| 7,951,151 B2 | 5/2011 | Butler |
| 7,967,822 B2 * | 6/2011 | Haines ............... A61B 17/155 |
| 7,967,824 B2 | 6/2011 | Thau et al. |
| 7,972,383 B2 | 7/2011 | Goldstein et al. |
| D642,678 S | 8/2011 | Dockstader et al. |
| D646,389 S | 10/2011 | Claypool et al. |
| 8,216,242 B2 | 7/2012 | Marchyn et al. |
| 8,628,560 B2 | 1/2014 | Moore et al. |
| 8,834,574 B2 | 9/2014 | Todd et al. |
| 8,951,262 B2 | 2/2015 | Kecman et al. |
| 9,033,989 B2 | 5/2015 | Wolfson |
| 9,125,749 B2 | 9/2015 | Amirouche et al. |
| 9,987,023 B2 | 6/2018 | Edwards |
| 10,022,130 B2 | 7/2018 | Edwards et al. |
| 10,111,673 B2 | 10/2018 | Edwards et al. |
| 10,335,163 B2 | 7/2019 | Christie et al. |
| 10,357,261 B2 | 7/2019 | Kugler et al. |
| 10,828,047 B2 | 11/2020 | Edwards et al. |
| 2002/0115987 A1 | 8/2002 | Hildwein et al. |
| 2003/0018338 A1 | 1/2003 | Axelson, Jr. et al. |
| 2003/0069586 A1 | 4/2003 | Errico et al. |
| 2003/0163137 A1 | 8/2003 | Smucket et al. |
| 2004/0153066 A1 | 8/2004 | Coon et al. |
| 2004/0162561 A1 | 8/2004 | Marchyn et al. |
| 2005/0209605 A1 | 9/2005 | Grimm et al. |
| 2005/0228393 A1 | 10/2005 | Williams et al. |
| 2005/0240196 A1 | 10/2005 | Davis et al. |
| 2006/0058886 A1 | 3/2006 | Wozencroft |
| 2006/0142777 A1 | 6/2006 | Bastian |
| 2007/0118141 A1 | 5/2007 | Marchyn et al. |
| 2007/0150066 A1 | 6/2007 | McMinn |
| 2007/0162031 A1 | 7/2007 | Hogg et al. |
| 2007/0177394 A1 | 8/2007 | Vock et al. |
| 2007/0179626 A1 | 8/2007 | de la Barrera et al. |
| 2007/0213738 A1 | 9/2007 | Martin et al. |
| 2007/0233142 A1 | 10/2007 | Oliver |
| 2007/0260227 A1 | 11/2007 | Phan |
| 2008/0097450 A1 | 4/2008 | Brown et al. |
| 2008/0114366 A1 | 5/2008 | Smucker et al. |
| 2008/0154269 A1 | 6/2008 | Roger et al. |
| 2008/0177394 A1 | 7/2008 | Chauhan |
| 2008/0221569 A1 | 9/2008 | Moore et al. |
| 2008/0228190 A1 | 9/2008 | Sherry et al. |
| 2008/0306484 A1 | 12/2008 | Coon et al. |
| 2009/0082774 A1 | 3/2009 | Oti |
| 2009/0088753 A1 | 4/2009 | Aram et al. |
| 2009/0222014 A1 | 9/2009 | Bojarski et al. |
| 2009/0264737 A1 | 10/2009 | Haechler et al. |
| 2009/0326661 A1 | 12/2009 | Wright et al. |
| 2010/0030223 A1 | 2/2010 | Keller |
| 2010/0121389 A1 | 5/2010 | Librot et al. |
| 2010/0152742 A1 | 6/2010 | Nevels et al. |
| 2010/0160924 A1 | 6/2010 | Soliman |
| 2010/0168752 A1 | 7/2010 | Edwards |
| 2010/0168753 A1 | 7/2010 | Edwards et al. |
| 2010/0191244 A1 | 7/2010 | White et al. |
| 2010/0204701 A1 | 8/2010 | Tallarida et al. |
| 2010/0249938 A1 | 9/2010 | Gunther et al. |
| 2012/0078261 A1 | 3/2012 | Kecman et al. |
| 2013/0023883 A1 | 1/2013 | Wright et al. |
| 2013/0023890 A1 | 1/2013 | Kecman et al. |
| 2013/0030443 A1 | 1/2013 | Wright et al. |
| 2013/0030539 A1 | 1/2013 | Wright et al. |
| 2013/0035693 A1 | 2/2013 | Wright et al. |
| 2013/0079787 A1 | 3/2013 | Spencer et al. |
| 2013/0079788 A1 | 3/2013 | Spencer et al. |
| 2013/0079789 A1 | 3/2013 | Randle et al. |
| 2013/0211410 A1 | 8/2013 | Landes et al. |
| 2013/0296871 A1 | 11/2013 | Lazar et al. |
| 2013/0325017 A1 | 12/2013 | Lomicka |
| 2014/0094818 A1 | 4/2014 | Wallace et al. |
| 2014/0257305 A1 | 9/2014 | Edwards et al. |
| 2017/0245906 A1 | 8/2017 | Kugler et al. |
| 2017/0245935 A1 | 8/2017 | Kugler et al. |

FOREIGN PATENT DOCUMENTS

| | | |
|---|---|---|
| CN | 101522144 A | 9/2009 |
| CN | 101617967 A | 1/2010 |
| CN | 201814648 U | 5/2011 |
| EP | 791335 A1 | 8/1997 |
| EP | 992222 A2 | 4/2000 |
| EP | 1723916 B1 | 7/2008 |
| EP | 1967143 A2 | 9/2008 |
| EP | 2039304 A2 | 3/2009 |
| EP | 2208469 A1 | 7/2010 |
| EP | 2319433 A1 | 5/2011 |
| EP | 2574314 A1 | 4/2013 |
| FR | 2737848 A1 | 2/1997 |
| GB | 2433695 A | 7/2007 |
| GB | 2433698 A | 7/2007 |
| JP | 2005253970 A | 9/2005 |
| JP | 2010158519 A | 7/2010 |
| WO | 9945856 A1 | 9/1999 |

(56) References Cited

FOREIGN PATENT DOCUMENTS

| WO | 9965403 | 12/1999 |
|---|---|---|
| WO | 2003071961 A1 | 9/2003 |
| WO | 2005110249 A1 | 11/2005 |
| WO | 2006027098 A1 | 3/2006 |
| WO | 2008108886 A2 | 9/2008 |
| WO | 2008112996 A1 | 9/2008 |
| WO | 2012024317 A2 | 2/2012 |
| WO | 2013003730 A1 | 1/2013 |

OTHER PUBLICATIONS

European Search Report and Opinion for App. No. 14157147.1-1654, dated Apr. 15, 2014.
Australian Examination Report No. 1 for Australian Application No. 2014201030 dated Dec. 9, 2017, 4 pages.
Japanese Search/Examination Report for Japanese Patent Application No. 2014-041288 dated Dec. 19, 2017, 6 pages. (Document not available).
SIGMA Fixed Bearing Surgical Technique by DePuy Orthopaedics, Inc. (2010).
Depuy International, Ltd., PFC SIGMA Rotating Platform Knee System With MBTTray, Surgical Technique Brochure, 2003 (43 Pages), CAT. No. 9068-96-000, Depuy International, Ltd., Leeds, England.
Depuy Orthopaedics, Inc., LCS High Performance Instruments, Surgical Technique Guide, 2008, (44 Pages), Pub. No. 0612-85-506, Depuy Orthopaedics, Inc., Warsaw, IN.
Depuy Orthopaedics, Inc. SIGMA High Performance Instruments, Classic Surgical Technique, 2010, (52 Pages), Pub. No. 0612-89-510, Depuy Orthopaedics, Inc., Warsaw, IN.
Depuy Orthopaedics, Inc., SIGMA High Performance Ins 1 Ruments, Design Rationale, 2007 (12 Pages), Pub. No. 0612-54-506 (Rev. 2), Depuy Orthopaedics, Inc., Warsaw, IN.
European Search Report, European Pat. App. No. 11175824.9-2310, Dec. 16, 2011 (7 Pages).
European Search Report, European Pat. App. No. 12191753.8-2310, Jan. 3, 2013 (6 Pages).
European Search Report for European Application No. 12174683.8-2310, Sep. 3, 2012 (6 Pages).
European Search Report for European Application No. 12174682.0-2310, Sep. 5, 2012 (6 Pages).
International Search Report, International Application No. PCT/US12/44947, Oct. 12, 2012 (3 Pages).
European Search Report for European Application No. 12186675.0-2310, Dec. 12, 2012 (7 Pages).
European Search Report for European Application No. 12186700.6-2310, Dec. 13, 2012 (8 Pages).
European Search Report for European Application No. 12186728.7-2310, Dec. 14, 2012 (8 Pages).
Extended European Search Report, European Application No. 16160477.2-1654, dated May 11, 2016 (8 Pages).
European Search Report for EPO App. No. 13186416.9-1654, Jan. 17, 2014 (7 Pages).
European Search Report for EPO App. No. 13186416.7-1654, Dec. 6, 2013 (7 Pages).

* cited by examiner

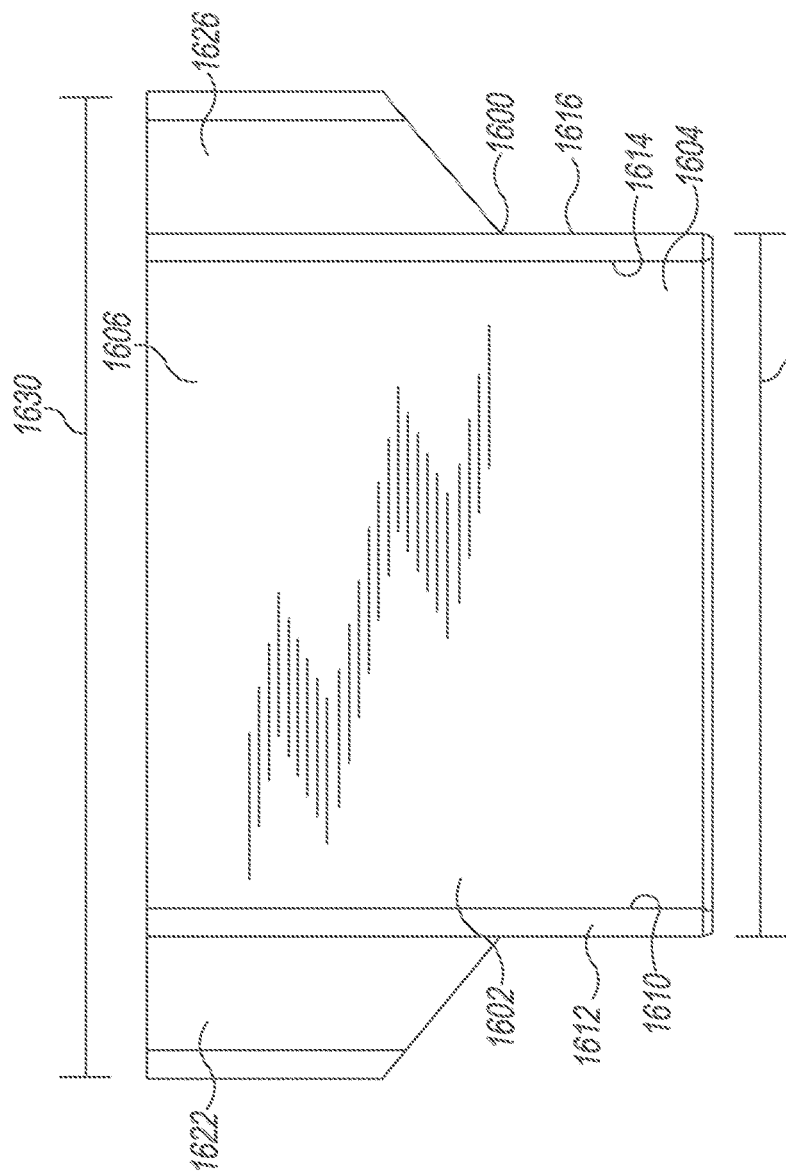
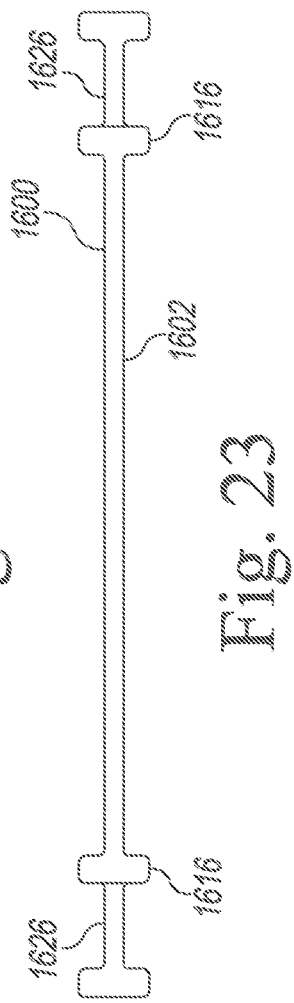
Fig. 22
Fig. 23

POLYMER CUTTING BLOCK

TECHNICAL FIELD

The present disclosure relates generally to orthopaedic surgical instruments and, more particularly, to cutting blocks used to resect a patient's bone.

BACKGROUND

Joint arthroplasty is a well-known surgical procedure by which a diseased and/or damaged natural joint is replaced by a prosthetic joint. Typical artificial joints include knee prostheses, hip prostheses, shoulder prostheses, ankle prostheses, and wrist prostheses, among others. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. In a hip replacement surgical procedure, a patient's natural acetabulum is replaced by a prosthetic cup and a patient's natural femoral head is partially or totally replaced by a prosthetic stem and femoral ball.

To facilitate the replacement of the natural joint with a prosthesis, orthopaedic surgeons use a variety of orthopaedic surgical instruments such as, for example, cutting blocks, drill guides, milling guides, and other surgical instruments. Typically, the orthopaedic surgical instruments are reusable and generic with respect to the patient such that the same orthopaedic surgical instrument may be used on a number of different patients during similar orthopaedic surgical procedures.

SUMMARY

According to an aspect of the present disclosure, a polymer 4-in-1 cutting block for performing an orthopedic surgical procedure on a distal end of a patient's femur includes a first polymer half-block and a second polymer half-block. The first polymer half-block may have a plurality of first cutting slots and a plurality of alignment receptacles formed in an inner sidewall of the first polymer half-block. The second polymer half-block separate from the first polymer half-block and configured to be coupled to the first polymer half-block to form an assembled polymer 4-in-1 cutting block. The second polymer half-block may include a plurality of second cutting slots and a plurality of alignment protrusions formed in an inner sidewall of the second polymer half-block. Additionally, when the second polymer half-block is coupled to the first polymer half-block, each of the first cutting slot cooperates with a corresponding second cutting slot to define a respective polymer cutting guide and each alignment protrusion is received in a corresponding alignment receptacle.

In some embodiments, the inner sidewall of the first polymer half-block may confront the inner sidewall of the second polymer half-block when the second polymer half-block is coupled to the first polymer half-block. Additionally, in some embodiments, when the second polymer half-block is coupled to the first polymer half-block, the plurality of first cutting slots and the plurality of second cutting slots cooperate to define an anterior polymer cutting guide and two polymer chamfer cutting guides. Furthermore, in some embodiments, the each respective polymer cutting guide is devoid of any metal inserts. Additionally, in some embodiments, an anterior edge of the inner sidewall of the first polymer half-block and an anterior edge of the inner sidewall of the second polymer half-block are both chamfered inwardly.

According to another aspect of the present disclosure, a method for fabricating a polymer cutting block for performing an orthopedic surgical procedure on a distal end of a patient's femur may include injection molding a first polymer half-block having a plurality of first cutting slots and a plurality of alignment receptacles formed in an inner sidewall of the first polymer half-block using a first injection mold and injection molding a second polymer half-block configured to be coupled to the first polymer half-block using a second injection mold. The second polymer half-block may include a plurality of second cutting slots and a plurality of alignment protrusions formed in an inner sidewall of the second polymer half-block. Additionally, each alignment protrusion may be configured to be received in a corresponding alignment receptacle of the first polymer half-block. The method may also include coupling the second polymer half-block to the first polymer half-block such that the inner sidewall of the first polymer half-block confronts the inner sidewall of the second polymer half-block.

In some embodiments, coupling the second polymer half-block to the first polymer half-block may include inserting each alignment protrusion of the second polymer half-block into a corresponding alignment receptacle of the first polymer half-block. Additionally, the method may also include securing the second polymer half-block and the first polymer half-block to each other. For example, the second polymer half-block and the first polymer half-block may be secured to each other using a metal securing device. The method may also include cleaning the first polymer half-block and the second polymer half-block prior to coupling the second polymer half-block to the first polymer half-block.

According to a further aspect of the present disclosure, a fabrication kit for fabricating a polymer 4-in-1 cutting block via an injection molding fabrication process may include an anterior cutting guide core, a first chamfer cutting guide core, and a second chamfer cutting guide core. The anterior cutting guide core may include a planar body including an anterior cutting guide molding end and a handle end opposite the anterior cutting guide molding end. The handle end may have a greater width than the anterior cutting guide molding end and the anterior cutting guide molding end may be configured to form an anterior polymer cutting guide of the polymer 4-in-1 cutting block during the injection molding fabrication process. The first chamfer cutting guide core may have a planar body including a first chamfer cutting guide molding end, a handle end opposite the first chamfer cutting guide molding end, and a slot defined through the first chamfer cutting guide molding end. The first chamfer cutting guide molding end may be configured to form a first chamfer cutting guide of the polymer 4-in-1 cutting block during the injection molding fabrication process. The second chamfer cutting guide core may have a planar body including a second chamfer cutting guide molding end and a handle end opposite the second chamfer cutting guide molding end. The second chamfer cutting guide molding end may be configured to be received through the slot of the planar body of the first chamfer cutting guide core and may form a second chamfer cutting guide of the polymer 4-in-1 cutting block during the injection molding fabrication process.

In some embodiments, the first chamfer cutting guide core may further include a medial side-rail attached to a medial side of the planar body of the first chamfer cutting guide core and a lateral side-rail attached to a lateral side of the planar body of the first chamfer cutting guide core. In such embodiments, the first chamfer cutting guide core may further include a medial stop flange attached to the medial side-rail toward the handle end of the planar body of the first chamfer cutting guide core and a lateral stop flange attached to the lateral side-rail toward the handle end of the planar body of the first chamfer cutting guide core.

In some embodiments, the second chamfer cutting guide core may further include a medial side-rail attached to a medial side of the planar body of the second chamfer cutting guide core and a lateral side-rail attached to a lateral side of the planar body of the second chamfer cutting guide core. The second chamfer cutting guide core may further include a medial stop flange attached to the medial side-rail toward the handle end of the planar body of the second chamfer cutting guide core, and a lateral stop flange attached to the lateral side-rail toward the handle end of the planar body of the second chamfer cutting guide core. Additionally, in some embodiments, each of the anterior cutting guide, the first chamfer cutting guide, and the second chamfer cutting guide may be formed from a metallic material.

According to yet a further aspect of the present disclosure, a method for fabricating a polymer 4-in-1 cutting block for performing an orthopedic surgical procedure on a distal end of a patient's femur may include coupling a first chamfer cutting guide core to a second chamfer cutting guide core to form an assembled chamfer cutting guide core, positioning an anterior cutting guide core into an injection mold of the polymer 4-in-1 cutting block, positioning the assembled chamfer cutting guide core into the injection mold; and performing an injection molding process to form the polymer 4-in-1 cutting block using the injection mold, the anterior cutting guide core, and the assembled chamfer cutting guide core. Each of the first and second chamfer cutting guide cores may include a planar body having a chamfer cutting guide molding end and a handle end opposite the chamfer cutting guide molding end. Additionally, the anterior cutting guide core may include a planar body having an anterior cutting guide molding end and a handle end opposite the anterior cutting guide molding end.

In some embodiments, the anterior cutting guide core molding end may form a polymer anterior cutting guide of the polymer 4-in-1 cutting block during the injection molding process. Additionally, each chamfer cutting guide molding end of the first and second chamfer cutting guide cores may form a polymer chamfer cutting guide of the polymer 4-in-1 cutting block during the injection molding process.

Additionally, in some embodiments, coupling the first chamfer cutting guide core to the second chamfer cutting guide core may include inserting the chamfer cutting guide molding end of the first chamfer cutting guide core through a slot defined in the chamfer cutting guide molding end of the second chamfer cutting guide core. In such embodiments, the method may further include removing the anterior cutting guide core molding end from the polymer 4-in-1 cutting block, removing the first chamfer cutting guide core from the polymer 4-in-1 cutting block by sliding the chamfer cutting guide molding end of the first chamfer cutting guide core from the slot defined in the chamfer cutting guide molding end of the second chamfer cutting guide core, and removing the second chamfer cutting guide core from the polymer 4-in-1 cutting block subsequent to the removal of the first chamfer cutting guide core.

According to an additional aspect of the present disclosure, a polymer 4-in-1 cutting block for performing an orthopedic surgical procedure on a distal end of a patient's femur may include a polymer body and a polymer chamfer cutting guide insert. The polymer body may include a bone-engaging side, an outer side opposite the bone engaging side, a polymer anterior cutting guide defined through the body, a polymer posterior cutting guide, and a chamfer cutting guide recess defined through the polymer body. The chamfer cutting guide recess may include a first opening defined on the outer side and a second opening, larger than the first opening, defined on the bone-engaging side. Additionally, the polymer chamfer cutting guide insert may be configured to be received in the chamfer cutting guide recess via the second opening to define a polymer chamfer cutting guide of the polymer 4-in-1 cutting block.

In some embodiments, the polymer body may further include a medial guide track defined on a medial side of the polymer body and a lateral guide track defined on a lateral side of the polymer body opposite the medial side. Additionally, the polymer chamfer cutting guide insert may further include a medial guide arm extending from a medial side of the polymer chamfer cutting guide insert and a lateral guide arm extending from a lateral side of the polymer chamfer cutting guide insert. In such embodiments, the medial guide arm may be configured to be received in the medial guide track and the lateral guide arm may be configured to be received in the lateral guide track when the polymer chamfer cutting guide insert is received in the chamfer cutting guide recess of the polymer body.

Additionally, in some embodiments, the polymer body may include a pair of threaded apertures and the polymer chamfer cutting guide insert may include a pair of non-threaded apertures defined therethough. In such embodiments, the polymer 4-in-1 cutting block may further include a pair of securing devices configured to be received into the non-threaded apertures of the polymer chamfer cutting guide insert and threaded into the threaded apertures of the polymer body to secure the polymer chamfer cutting guide insert to the polymer body.

In some embodiments, the polymer chamfer cutting guide insert may have a triangular cross-section. Additionally, in some embodiments, the polymer chamfer cutting guide insert and the polymer body may cooperate to define an anteriorly-angled polymer chamfer cutting guide and a posteriorly-angled polymer chamfer cutting guide when the polymer chamfer cutting guide insert is received in the chamfer cutting guide recess of the polymer body.

According to yet another aspect of the present disclosure, a method for performing an orthopaedic surgical procedure on a distal end of a patient's femur may include assembling a polymer 4-in-1 cutting block by inserting a polymer chamfer cutting guide insert into a chamfer cutting guide recess of a polymer body, securing the assembled polymer 4-in-1 cutting block to a surgically prepared distal end of the patient's femur, and performing a femoral resection procedure on the patient's femur using the assembled polymer 4-in-1 cutting block. In some embodiments, the polymer body may include a polymer anterior cutting guide and a polymer posterior cutting guide.

In some embodiments, the chamfer cutting guide recess may include a first opening defined on an outer side of the polymer body and a second opening, larger than the first opening, defined on a bone-engaging side of the polymer body. In such embodiments, assembling the polymer 4-in-1 cutting block may include inserting the polymer chamfer cutting guide insert into chamfer cutting guide recess of the polymer body via the second opening. Additionally, in such embodiments, securing the assembled polymer 4-in-1 cutting block may include abutting the bone-engaging side of the polymer body to the surgically prepared distal end of the patient's femur such that the polymer chamfer cutting guide insert is in contact with the patient's femur.

In some embodiments, assembling the polymer 4-in-1 cutting block may include inserting a pair of guide arms of the polymer chamfer cutting guide insert into a corresponding pair of guide tracks of the polymer body. In such embodiments, the method may further include securing the polymer chamfer cutting guide insert to the polymer body using a plurality of securing devices.

According to a further aspect of the present disclosure, a fabrication kit for fabricating a polymer 4-in-1 cutting block via an injection molding fabrication process may include a sacrificial anterior cutting guide core and a sacrificial chamfer cutting guide core. The sacrificial anterior cutting guide core may be configured to form an anterior polymer cutting guide of the polymer 4-in-1 cutting block during the injection molding fabrication process. The sacrificial chamfer cutting guide core may include a first cutting guide core and a second cutting guide core. The first and second cutting guide cores may extend through each other at an oblique angle relative to each other. Additionally, the sacrificial chamfer cutting guide core may be configured to form a polymer chamfer cutting guide of the polymer 4-in-1 cutting block during the injection molding fabrication process. In some embodiments, the sacrificial anterior cutting guide core and the sacrificial chamfer cutting guide core may be formed from a metal material having a melting point lower than a polymer from which the polymer 4-in-1 cutting block is formed.

Additionally, in some embodiments, the sacrificial anterior cutting guide core and the sacrificial chamfer cutting guide core may be formed from a metal alloy having a melting point of 550 degrees Fahrenheit or less. Furthermore, in some embodiments, the sacrificial anterior cutting guide core may include an elongated body having a first end, a second end opposite the first end, and a cutting guide molding section defined between the first end and the second end. The cutting guide molding section may have a thickness that is greater than a thickness of each of the first and second ends.

In some embodiments, the cutting guide molding section may have a shorter width than the each of the first and second ends. Additionally, in some embodiments, the first and second cutting guide cores of the sacrificial chamfer cutting guide core may include an elongated body having a first end, a second end opposite the first end, and a cutting guide molding section defined between the first end and the second end. In such embodiments, each cutting guide molding section may have a thickness that is greater than a thickness of the corresponding first and second ends.

According to yet a further aspect of the present disclosure, a method for fabricating a polymer 4-in-1 cutting block for performing an orthopedic surgical procedure on a distal end of a patient's femur may include positioning a sacrificial anterior cutting guide core and a sacrificial chamfer cutting guide core into a polymer 4-in-1 cutting block mold, injecting a polymer into the mold to form the polymer 4-in-1 cutting block, and melting the sacrificial anterior cutting guide core and a sacrificial chamfer cutting guide core to produce the polymer 4-in-1 cutting block. Each of the sacrificial anterior cutting guide core and a sacrificial chamfer cutting guide core has a melting point lower than the polymer.

In some embodiments, injecting the polymer into the mold may include forming a polymer anterior cutting guide of the polymer 4-in-1 cutting block using the sacrificial anterior cutting guide core and forming a polymer chamfer cutting guide using the sacrificial chamfer cutting guide core. Additionally, in some embodiments, melting the sacrificial anterior cutting guide core and a sacrificial chamfer cutting guide core may include subjecting the polymer 4-in-1 cutting block including the sacrificial anterior cutting guide core and a sacrificial chamfer cutting guide core to a temperature of at least 550 degrees Fahrenheit.

Furthermore, in some embodiments, melting the sacrificial anterior cutting guide core and a sacrificial chamfer cutting guide core may include immersing the polymer 4-in-1 cutting block into a liquid bath having a temperature of at least 550 degrees Fahrenheit. Additionally, in some embodiments, each of the sacrificial anterior cutting guide core and the sacrificial chamfer cutting guide core is formed from a metal alloy having a melting point of 550 degrees Fahrenheit or less. In such embodiments, the method may further include reclaiming the metal alloy subsequent to melting the sacrificial anterior cutting guide core and a sacrificial chamfer cutting guide core.

BRIEF DESCRIPTION OF THE DRAWINGS

The detailed description particularly refers to the following figures, in which:

FIG. 22 is a top plan view of the anterior chamfer cutting guide core;

FIG. 23 is an end elevation view of the anterior chamfer cutting guide core of FIG. 22;

DETAILED DESCRIPTION OF THE DRAWINGS

Figure 1:
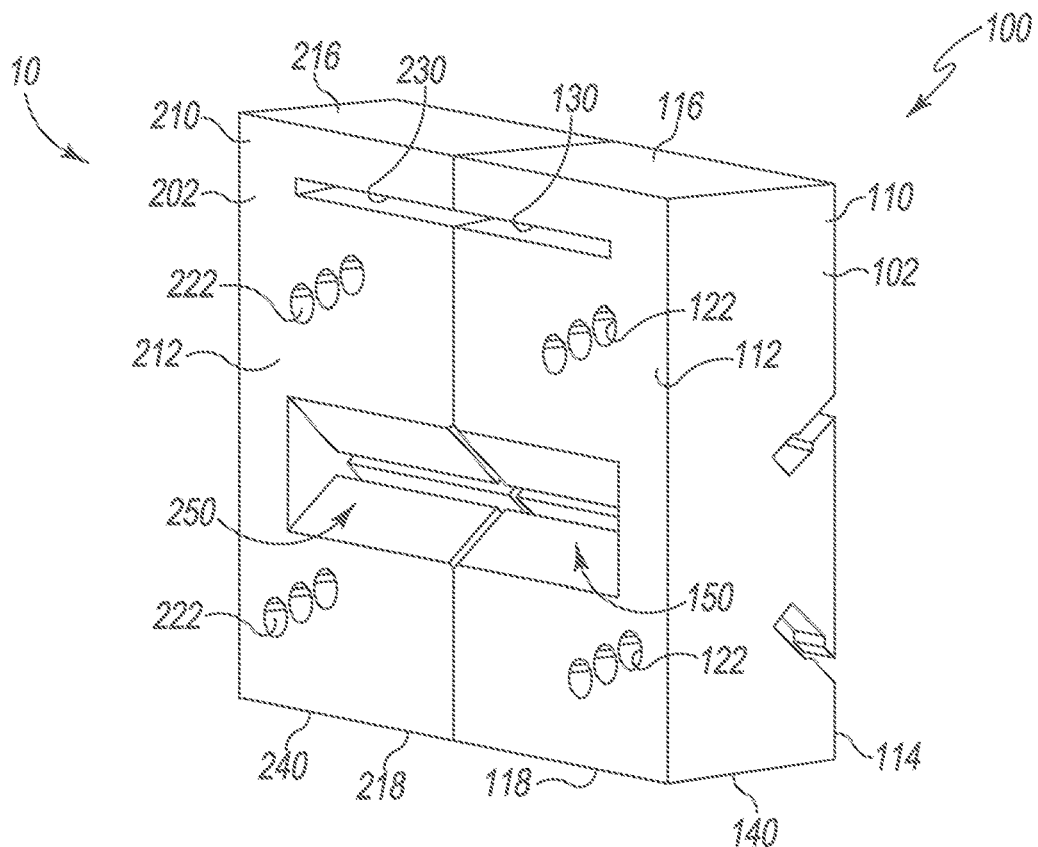
FIG. 1 is a perspective, elevation view of an embodiment of an all-polymer 4-in-1 cutting block showing an outer surface of the all-polymer 4-in-1 cutting block.
Figure 2:
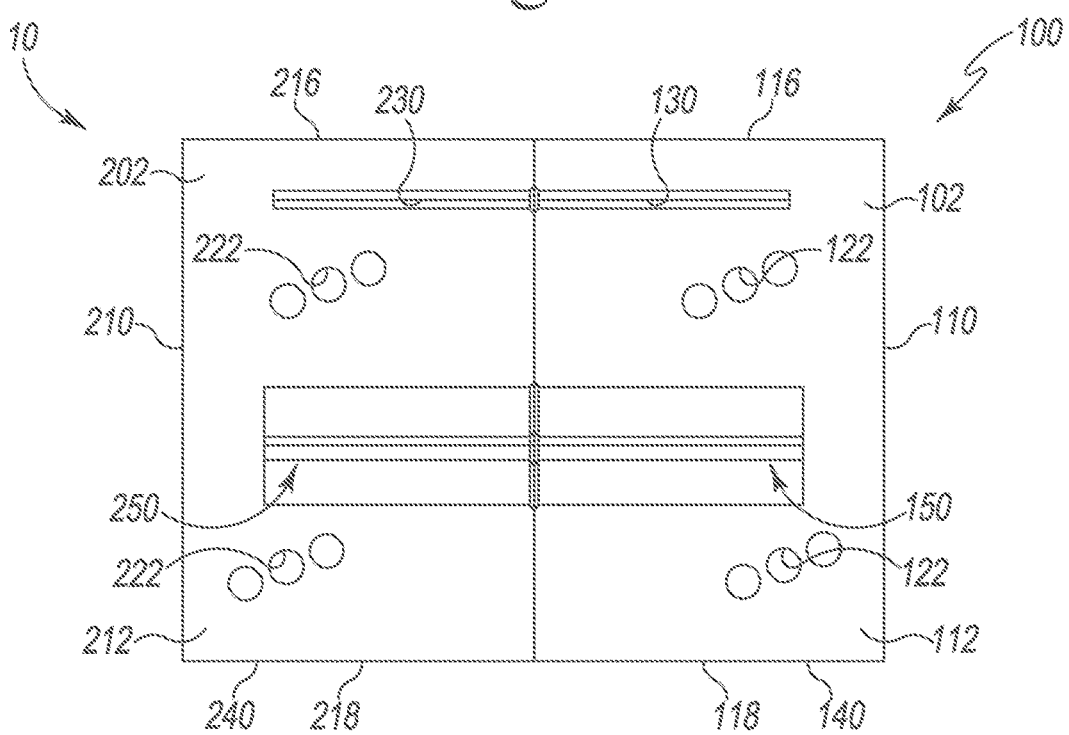
FIG. 2 is an elevation view of the all-polymer 4-in-1 cutting block of FIG. 1 showing the outer surface.
Figure 3:
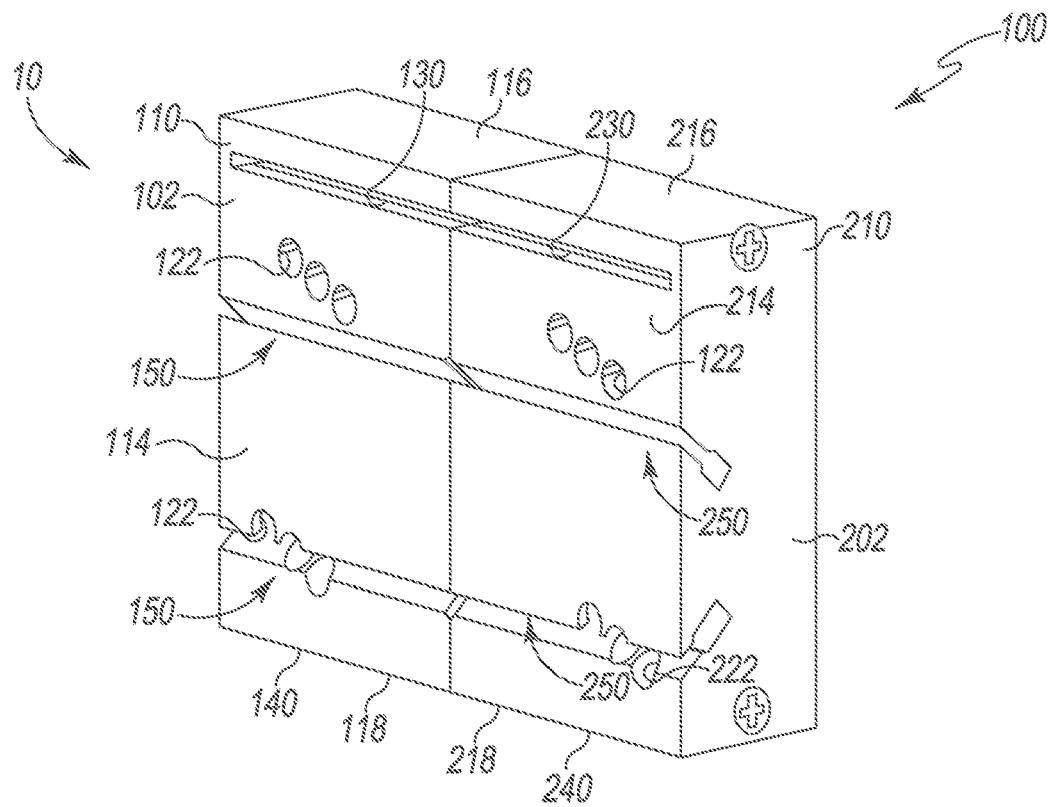
FIG. 3 is a perspective, elevation view of the all-polymer 4-in-1 cutting block of FIG. 1 showing a bone-engaging surface.
Figure 4:
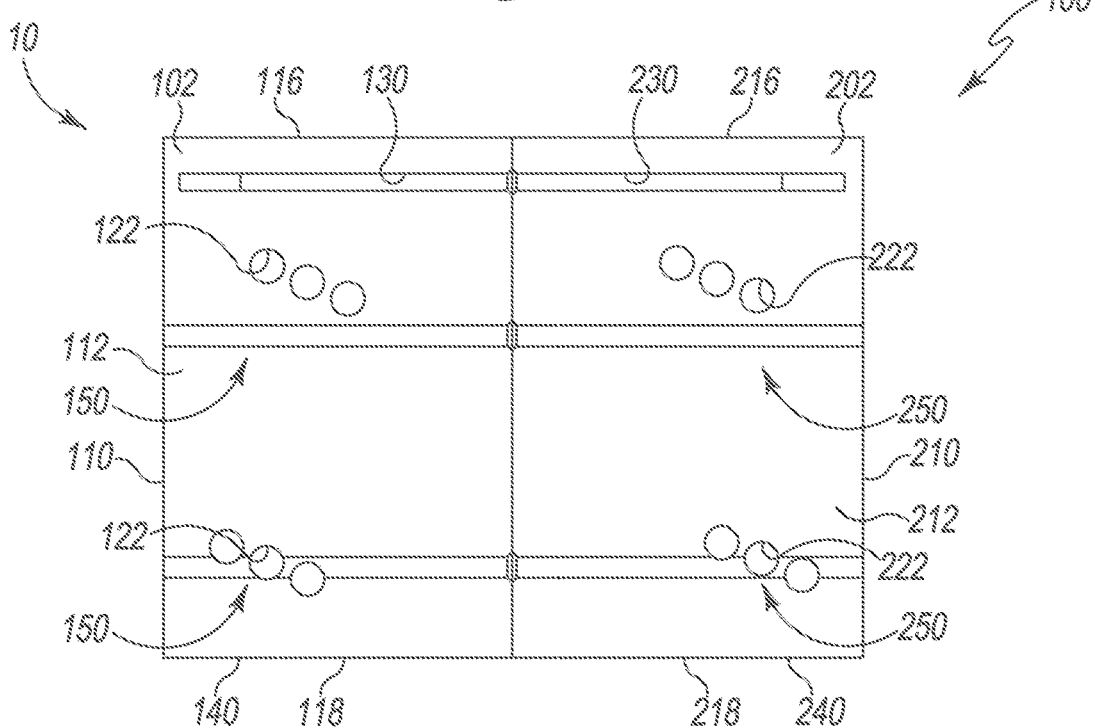
FIG. 4 is an elevation view of the all-polymer 4-in-1 cutting block of FIG. 1 showing the bone-engaging surface.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring initially to the figures in general, various embodiments of a single use orthopaedic surgical instrument are described below. As its name implies, the described single use orthopaedic surgical instrument is intended to be disposed of after use in a single orthopaedic surgical procedure. In the illustrative embodiments described herein, the orthopaedic surgical instrument is embodied as a single use all-polymer 4-in-1 cutting block for use in the surgical preparation of the patient's distal femur during a knee replacement procedure. As described in more detail below, each of the described embodiments of the single use all-polymer 4-in-1 cutting block may be used to perform various cuts of the distal end of the patient's femur, including an anterior cut, a posterior cut, and two chamfer cuts.

In each of the embodiments described below, the single use all-polymer 4-in-1 cutting block is formed using a corresponding injection molding procedure. As such, each of the described all-polymer 4-in-1 cutting blocks is formed from a polymer material. However, because the described 4-in-1 cutting blocks are designed to be all-polymer, certain design features are considered to facilitate the fabrication of the all-polymer 4-in-1 cutting blocks. An initial consideration is the particular polymer material used to form the all-polymer 4-in-1 cutting blocks. The polymer material may be selected so as to have a suitable rigidity and resistance to wear and debris production during the bone cutting procedures. For example, in some embodiments, the described all-polymer 4-in-1 cutting blocks may be formed from a polyetherimide-based resin that has been alloyed with a lubricant to minimize wear and with carbon fiber to increase strength and dimensional stability. However, in other embodiments, other types of polymers may be used to form the described all-polymer 4-in-1 cutting blocks. Another consideration is the geometrical design of each component of the various embodiments of the all-polymer 4-in-1 cutting block. That is, the particular shape and size of each component is selected to ensure each component can be properly fabricated from an injection molding procedure, while also properly coupling with other components to produce an assembled all-polymer 4-in-1 cutting block as described in more detail below.

Figure 47:
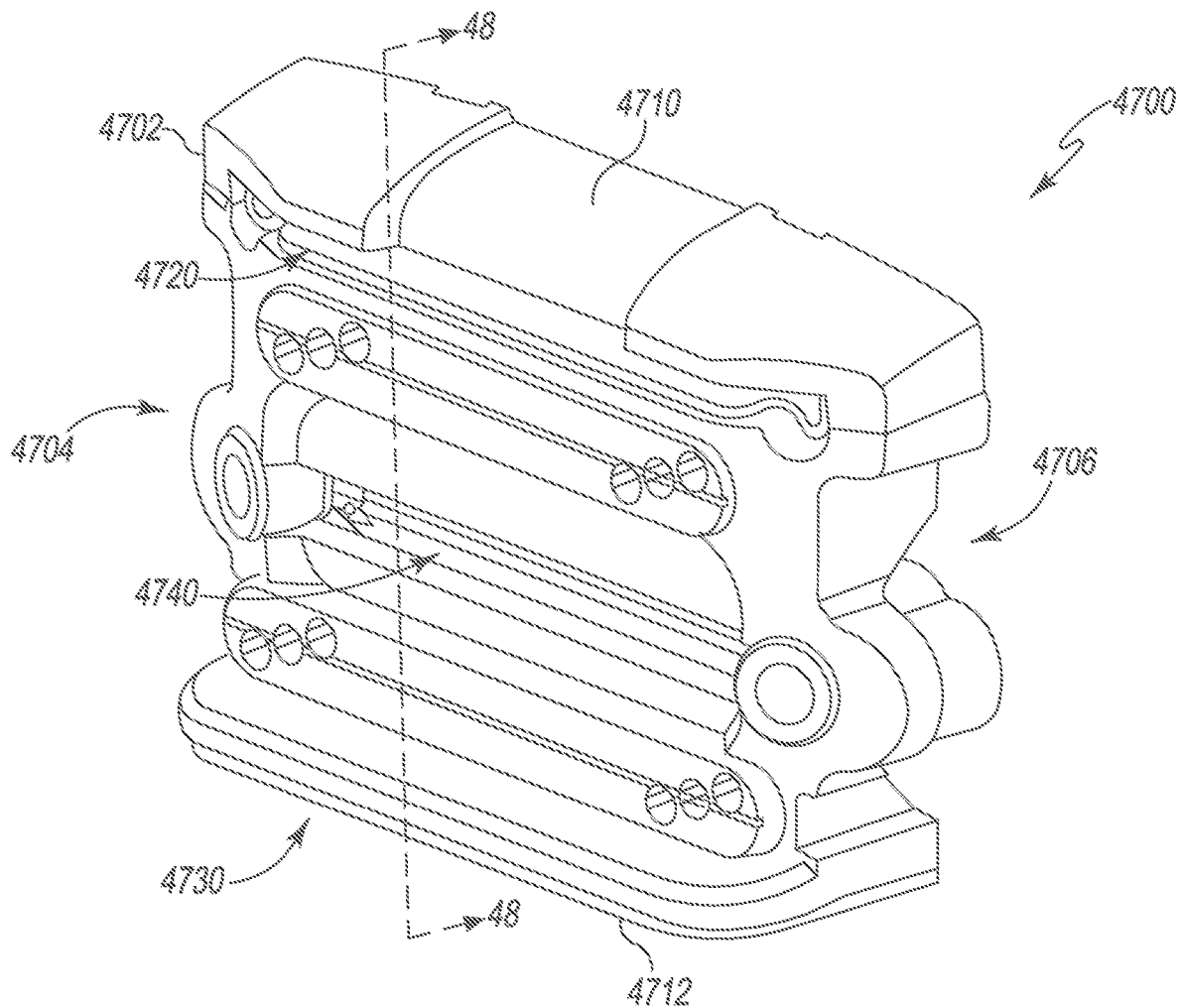
FIG. 47 is a perspective view of a typical polymer 4-in-1 cutting block.
Figure 48:
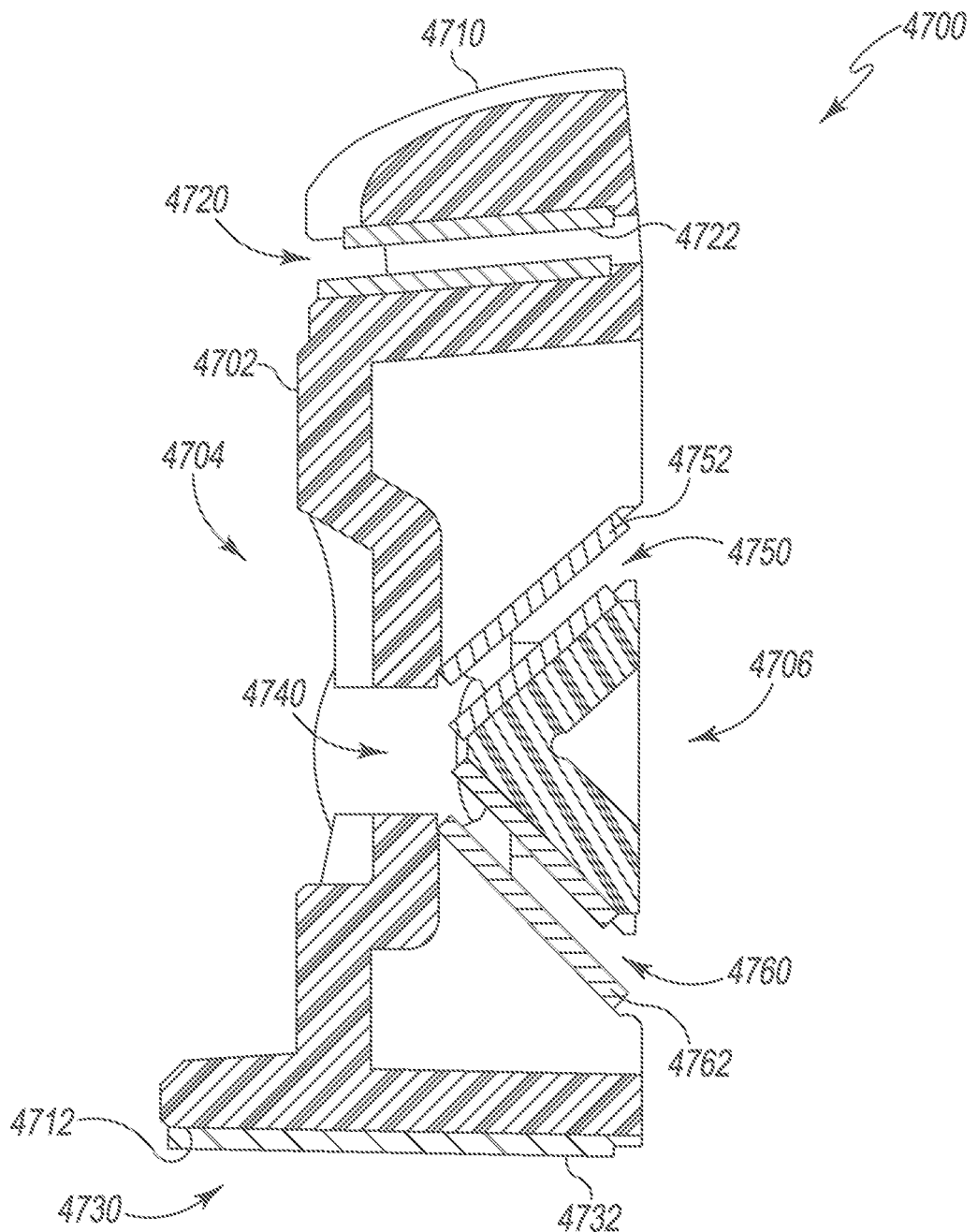
FIG. 48 is a cross-sectional view of the typical polymer 4-in-1 cutting block of FIG. 47 taken generally along line 48-48 of FIG. 47.

It should be appreciated that each of the described embodiments of the all-polymer 4-in-1 cutting block differ from typical polymer cutting blocks in that they are devoid of any metal inserts, which are typically used to form the metal cutting guides. For example, a typical polymer 4-in-1 cutting block 4700 is shown in FIGS. 47 and 48. The polymer 4-in-1 cutting block 4700 includes a body 4702 having an outer surface 4704 and a bone-engaging surface 4706 opposite the outer surface 4704. The polymer 4-in-1 cutting block 4700 also includes a number of cutting guides, each formed from a corresponding metallic insert. For example, the polymer 4-in-1 cutting block 4700 includes an anterior cutting slot 4720 defined in the body 4702 toward an anterior end 4710 of the body 4702. The anterior cutting slot 4720 is embodied as an elongated slot that extends in the medial/lateral direction and extends completely through the body 4702 (i.e., from the outer surface 4704 to the bone-engaging surface 4706). A metallic anterior cutting guide 4722 is secured within the anterior cutting slot 4720. The metallic anterior cutting guide 4722 is embodied as a captured cutting guide (i.e., it is closed on the anterior, posterior, medial, and lateral sides so as to capture a saw blade therein).

The polymer 4-in-1 cutting block 4700 also includes a posterior cutting surface 4730 formed on the body 4702 toward a posterior end 4712 of the body 4702. The posterior cutting surface 4730 is embodied as an elongated surface that extends in the medial/lateral direction and extends completely across the body 4702 (i.e., from the outer surface 4704 to the bone-engaging surface 4706). A metallic posterior cutting guide 4732 is secured to the posterior cutting surface 4730. The metallic posterior cutting guide 4732 is embodied as a non-captured cutting guide, but may be embodied as a captured cutting guide in some embodiments.

Additionally, the polymer 4-in-1 cutting block 4700 includes a chamfer cutting slot 4740 defined in the body 4702 toward its middle section, between the anterior cutting slot 4720 and the posterior cutting surface 4730. The chamfer cutting slot 4740 is embodied as an elongated slot that extends in the medial/lateral direction and extends completely through the body 4702 (i.e., from the outer surface 4704 to the bone-engaging surface 4706). The chamfer cutting slot 4740 includes an anteriorly angled cutting slot 4750 and a posteriorly angled cutting slot 4760, which extend away from each other as shown best in FIG. 48. A metallic chamfer cutting guide 4752 is secured within the anteriorly angled cutting slot 4750, and a metallic chamfer cutting guide 4762 is secured within the posteriorly angled cutting slot 4760. Each of the metallic chamfer cutting guides 4752, 4762 is embodied as a capture cutting guide, but may be embodied as a non-captured cutting guide in other embodiments.

Each of the metallic cutting guides 4722, 4732, 4752, 4762 is sized and shaped to receive, or otherwise support, a surgical saw or other cutting instrument and properly orient the cutting blade to resect the corresponding area of the patient's femur during an orthopaedic surgical procedure. The metallic cutting guides 4722, 4732, 4752, 4762 protect the polymer body 4702 of the polymer 4-in-1 cutting block 4700, which is typically formed from a soft polymer material, from the saw blade during the orthopaedic surgical procedure. However, the inclusion of the metallic cutting guides 4722, 4732, 4752, 4762 can increase the overall fabrication cost and complexity of the polymer 4-in-1 cutting block 4700 and limit or restrict the use of injection molding techniques to form the polymer 4-in-1 cutting block 4700.

Referring now to FIGS. 1-9, in an illustrative embodiment, an orthopaedic surgical instrument 10 is embodied as an all-polymer 4-in-1 cutting block 100. The illustrative all-polymer 4-in-1 cutting block 100 includes a "plug" polymer half-block 102 and a "jack" polymer half-block 202, which are sized and shaped to couple to each other as described in more detail below. Each of the plug polymer half-block 102 and the jack polymer half-block 202 form roughly one half of the all-polymer 4-in-1 cutting block 100. As such, the plug polymer half-block 102 and the jack polymer half-block 202 have a similar size and shape in the illustrative embodiment, but may be differently sized and/or shaped in other embodiments.

Figure 6:
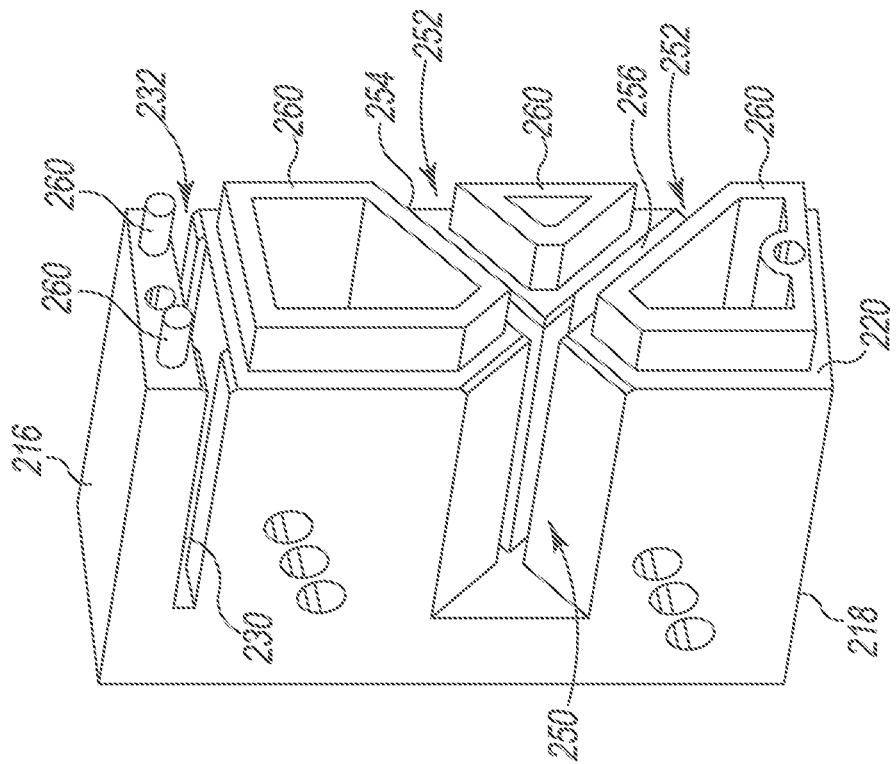
FIG. 6 is a perspective view of a jack half-block of the all-polymer 4-in-1 cutting block of FIG. 1 showing a number of alignment protrusions extending from an inner sidewall.
Figure 5:
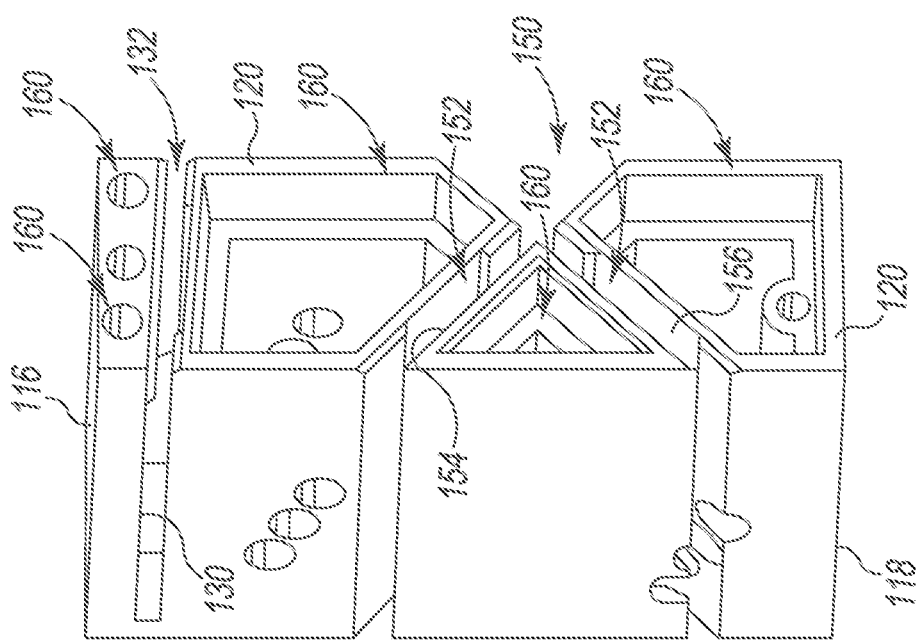
FIG. 5 is a perspective view of a plug half-block of the all-polymer 4-in-1 cutting block of FIG. 1 showing a number of alignment receptacles defined in an inner sidewall.

The plug polymer half-block 102 includes a polymer body 110 having an outer surface 112 and a bone-engaging surface 114 opposite the outer surface 112. The plug polymer half-block 102 also includes an anterior end 116, a posterior end 118 opposite the anterior end 116, and an inner sidewall 120 as shown in FIG. 5. Similarly, the jack polymer half-block 202 includes a polymer body 210 having an outer surface 212 and a bone-engaging surface 214 opposite the outer surface 212. The jack polymer half-block 202 also includes an anterior end 216, a posterior end 218 opposite the anterior end 216, and an inner sidewall 220 as shown in FIG. 6. Additionally, each of the polymer bodies 110, 210 includes a number of mounting apertures 122, 222, respectively, defined therethrough and configured to facilitate the attachment of the all-polymer 4-in-1 cutting block 100 to a distal end of the patient's surgically-prepared femur using corresponding securing devices, such as bone screws.

Each polymer half-block 102, 202 includes a number of cutting slots, which cooperate to define cutting guides when the polymer half-blocks 102, 202 are coupled together as discussed below. For example, the plug polymer half-block 102 includes an anterior cutting slot 130 defined in the polymer body 110 toward the anterior end 116 of the polymer body 110. The anterior cutting slot 130 is embodied as an open-ended, elongated slot that extends in the medial/lateral direction and includes an opened end 132 defined on the inner sidewall 120 of the polymer body 110 as best shown in FIG. 5. The anterior cutting slot 130 extends completely through the polymer body 110 (i.e., from the outer surface 112 to the bone-engaging surface 114).

Additionally, the plug polymer half-block 102 includes a posterior cutting surface 140 formed on the polymer body 110 toward the posterior end 118 of the polymer body 110. The posterior cutting surface 140 is embodied as an elongated surface that extends in the medial/lateral direction, ending at the inner sidewall 120 as shown in FIG. 5. The posterior cutting surface 140 also extends completely through the polymer body 110 (i.e., from the outer surface 112 to the bone-engaging surface 114).

The plug polymer half-block 102 also includes a chamfer cutting slot 150 defined in the polymer body 110 toward its middle section, between the anterior cutting slot 130 and the posterior cutting surface 140. The chamfer cutting slot 150 is embodied as an open-ended, elongated slot that extends in the medial/lateral direction and includes an opened end 152 defined on the inner sidewall 120 of the polymer body 110 as best shown in FIG. 5. Similar to the anterior cutting slot 130, the chamfer cutting slot 150 extends completely through the polymer body 110 (i.e., from the outer surface 112 to the bone-engaging surface 114). The chamfer cutting slot 150 includes an anteriorly angled cutting slot 154 and a posteriorly angled cutting slot 156, which extend away from each other as shown best in FIG. 5.

Similar to the plug polymer half-block 102, the jack polymer half-block 202 includes an anterior cutting slot 230 defined in the polymer body 210 toward the anterior end 216 of the polymer body 210. Similar to the anterior cutting slot 130 of the plug polymer half-block 102, the anterior cutting slot 230 is embodied as an open-ended, elongated slot that extends in the medial/lateral direction and includes an opened end 232 defined on the inner sidewall 220 of the polymer body 210 as best shown in FIG. 6. The anterior cutting slot 230 extends completely through the polymer body 210 (i.e., from the outer surface 212 to the bone-engaging surface 214).

Additionally, the jack polymer half-block 202 includes a posterior cutting surface 240 formed on the polymer body 210 toward the posterior end 218 of the polymer body 210. Similar to the posterior cutting surface 140 of the plug polymer half-block 102, the posterior cutting surface 240 is embodied as an elongated surface that extends in the medial/lateral direction, ending at the inner sidewall 220 as shown in FIG. 6. The posterior cutting surface 240 also extends completely through the polymer body 210 (i.e., from the outer surface 212 to the bone-engaging surface 214).

The jack polymer half-block 202 also includes a chamfer cutting slot 250 defined in the polymer body 210 toward its middle section, between the anterior cutting slot 230 and the posterior cutting surface 240. Again, similar to the anterior cutting slot 130 of the plug polymer half-block 102, the chamfer cutting slot 250 is embodied as an open-ended, elongated slot that extends in the medial/lateral direction and includes an opened end 252 defined on the inner sidewall 220 of the polymer body 210 as best shown in FIG. 6. The chamfer cutting slot 250 extends completely through the polymer body 210 (i.e., from the outer surface 212 to the bone-engaging surface 214). The chamfer cutting slot 250 includes an anteriorly angled cutting slot 254 and a posteriorly angled cutting slot 256, which extend away from each other as shown best in FIG. 6.

Figure 8:
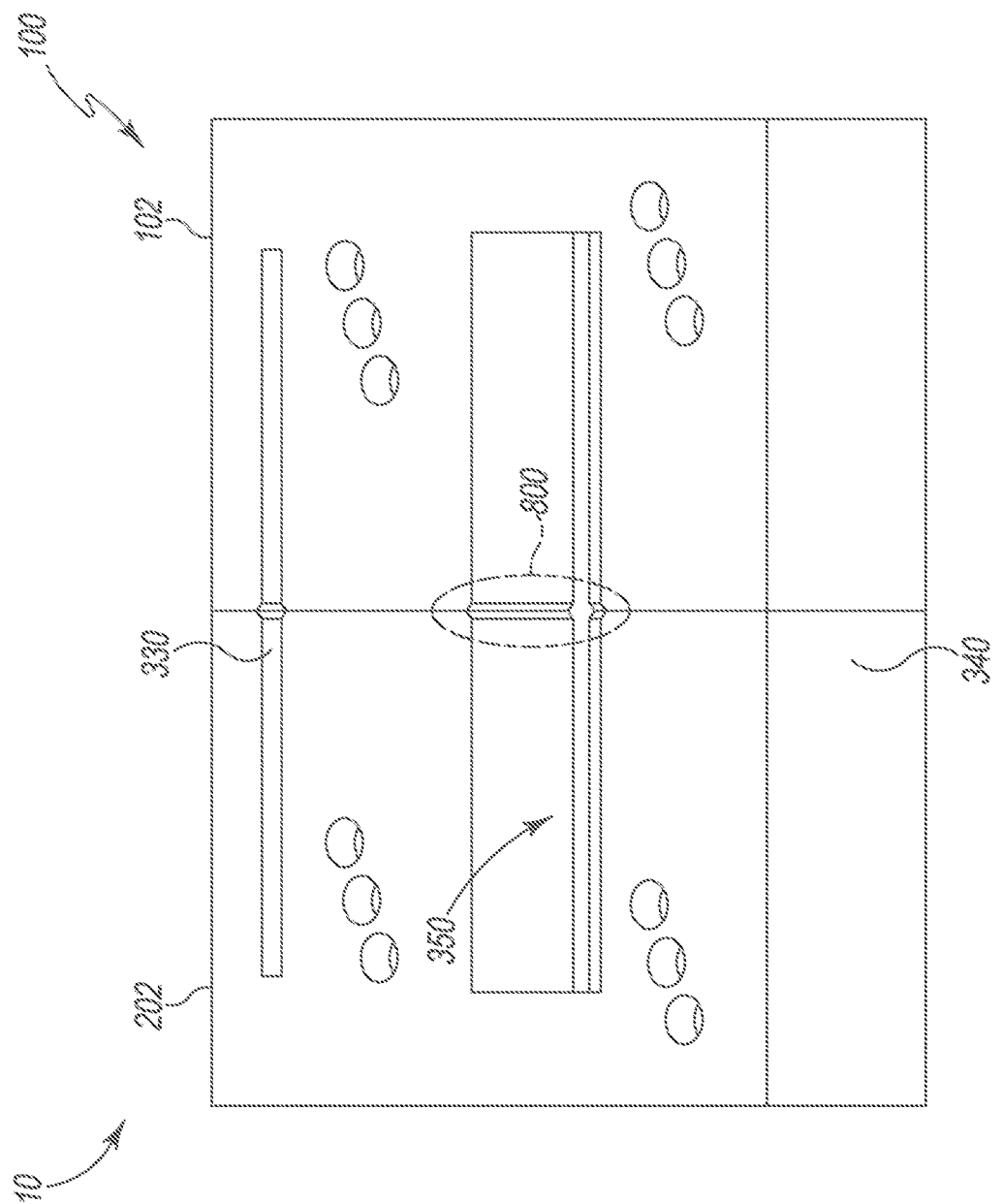
FIG. 8 is an inferior-perspective view of the all-polymer 4-in-1 cutting block of FIG. 1 showing the outer surface.

When the jack polymer half-block 202 is coupled to the plug polymer half-block 102, the various cutting slots of the polymer half-blocks 102, 202 cooperate to define corresponding polymer cutting guides. For example, the anterior cutting slot 130 of the plug polymer half-block 102 is brought into fluid communication with the anterior cutting slot 230 of the jack polymer half-block 202, and the anterior cutting slots 130, 230 cooperate to define a polymer anterior cutting guide 330, when the polymer half-blocks 102, 202 are coupled together as best shown in FIG. 8. Similarly, the posterior cutting surface 140 of the plug polymer half-block 102 is abutted to the posterior cutting surface 240 of the jack polymer half-block 202, and the posterior cutting surfaces 140, 240 cooperate to define a polymer posterior cutting guide 340, when the polymer half-blocks 102, 202 are coupled together as best shown in FIG. 8. Additionally, the chamfer cutting slot 150 of the plug polymer half-block 102 is brought into fluid communication with the chamfer cutting slot 250 of the jack polymer half-block 202, and the chamfer cutting slots 150, 250 cooperate to define polymer chamfer cutting guide 350, when the polymer half-blocks 102, 202 are coupled together as best shown in FIG. 8.

It should be appreciated that the polymer cutting guides 330, 340, 350 are devoid of any metallic cutting inserts or guides as used in typical polymer cutting blocks. Rather, each of the polymer cutting guides 330, 340, 350 is sized and shaped to receive, or otherwise support, a surgical saw or other cutting instrument, without the use of a metallic cutting insert, and properly orient the cutting blade to resect the corresponding area of the patient's femur during an orthopaedic surgical procedure. To reduce the likelihood of the saw blade catching at the seam of the polymer half-blocks 102, 202, the edge of each cutting slot/surface 130, 140, 150, 230, 240, 250 at the corresponding inner sidewall 120, 220 may be chamfered inwardly as illustratively shown via area 800 in FIG. 8.

To facilitate the coupling of the plug polymer half-block 102 and the jack polymer half-block 202, each of the polymer half-blocks 102, 202 includes alignment features defined on/in their respective inner sidewalls 120, 220. For example, as shown in FIG. 5, the plug polymer half-block 102 includes a number of alignment receptacles 160 defined in the inner sidewall 120. Some of the alignment receptacles 160 may have simple geometric shape such as the cylindrical-shaped alignment receptacles 160 located toward the anterior end 116 of the polymer body 110, while other alignment receptacles 160 may have complex geometric shapes. For example, some of the alignment receptacles 160 have a complex shape defined by the anterior cutting slot 130, the posterior cutting surface 140, and the chamfer cutting slot 150 as shown in FIG. 5.

Conversely, as shown in FIG. 6, the jack polymer half-block 202 includes a number of alignment protrusions 260 that extend from the inner sidewall 220. Some of the alignment protrusions 260 may have simple geometric shape such as the cylindrical-shaped alignment protrusions 260 located toward the anterior end 216 of the polymer body 210, while other alignment protrusions 260 may have complex geometric shapes. For example, some of the alignment protrusions 260 have a complex shape defined by the anterior cutting slot 230, the posterior cutting surface 240, and the chamfer cutting slot 250 as shown in FIG. 6.

Figure 7:
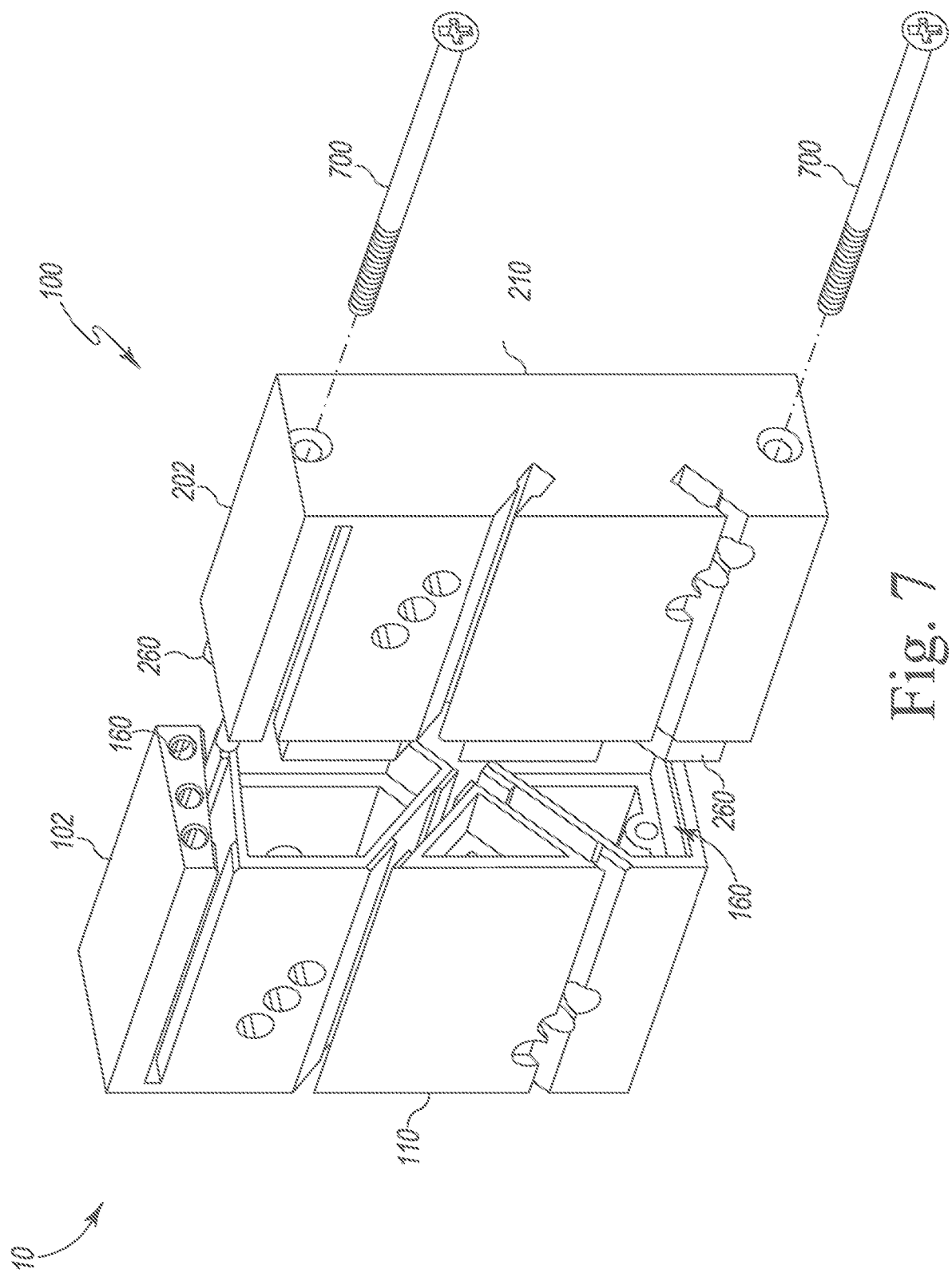
FIG. 7 is an exploded perspective view of the all-polymer 4-in-1 cutting block of FIG. 1.

As shown in FIG. 7, the plug polymer half-block 102 and the jack polymer half-block 202 may be coupled together by inserting the alignment protrusions 260 of the jack polymer half-block 202 into the corresponding alignment receptacles 160 of the plug polymer half-block 102. When the polymer half-blocks 102, 202 are coupled in this manner, the inner sidewall 120 of the plug polymer half-block 102 confronts the inner sidewall 220 of the jack polymer half-block 202. The polymer half-blocks 102, 202 may be subsequently secured to each other via use of one or more securing devices 700, which may be formed from a metallic material such as, for example, steel, titanium alloy, or cobalt chromium alloy.

Figure 9:
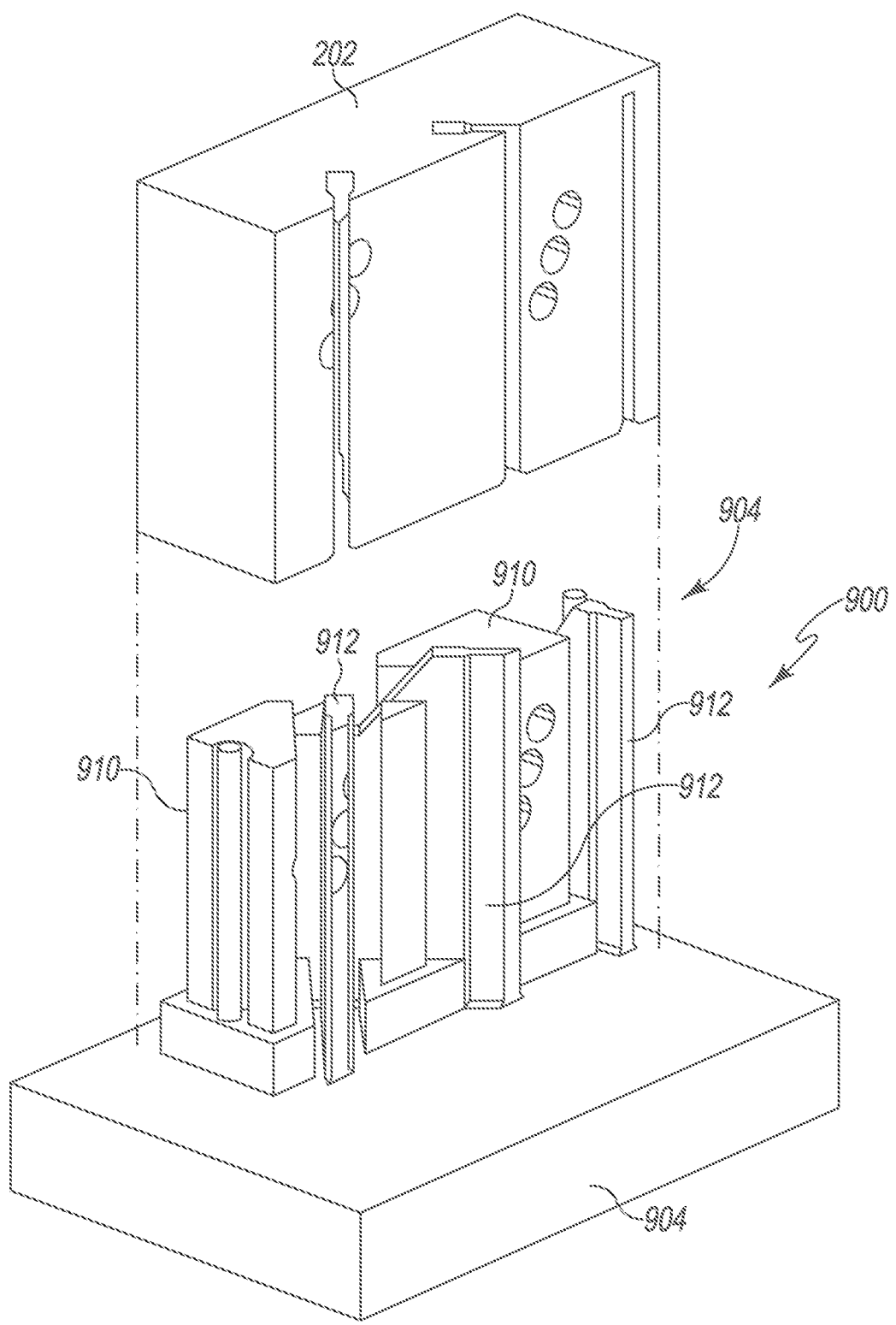
FIG. 9 is a perspective view of the jack half-block of FIG. 7 being removed from an injection mold subsequent to an injection molding procedure used to form the jack half-block.

Referring now to FIG. 9, each of the plug polymer half-block 102 and the jack polymer half-block 202 may be fabricated via an injection molding process. To do so, a corresponding molding core 900 for each polymer half-block 102, 202 may be used. The molding core 900 may be formed any suitable material capable of withstanding the temperatures associated with the injection molding process. For example, in the illustrative embodiment, the molding core 900 is formed from a metallic material such as, for example, steel or a titanium alloy.

Each molding core 900 includes a number of negative mold features 902, each of which extends from a base 904. The negative mold features 902 include body features 910, which are sized, shaped, and position to define the various walls of the polymer bodies 110, 210. Additionally, the negative mold features 902 include cutting slot features 912, which are sized, shaped, and position to define the anterior cutting slots 130, 230 and the chamfer cutting slots 150, 250.

Figure 10:
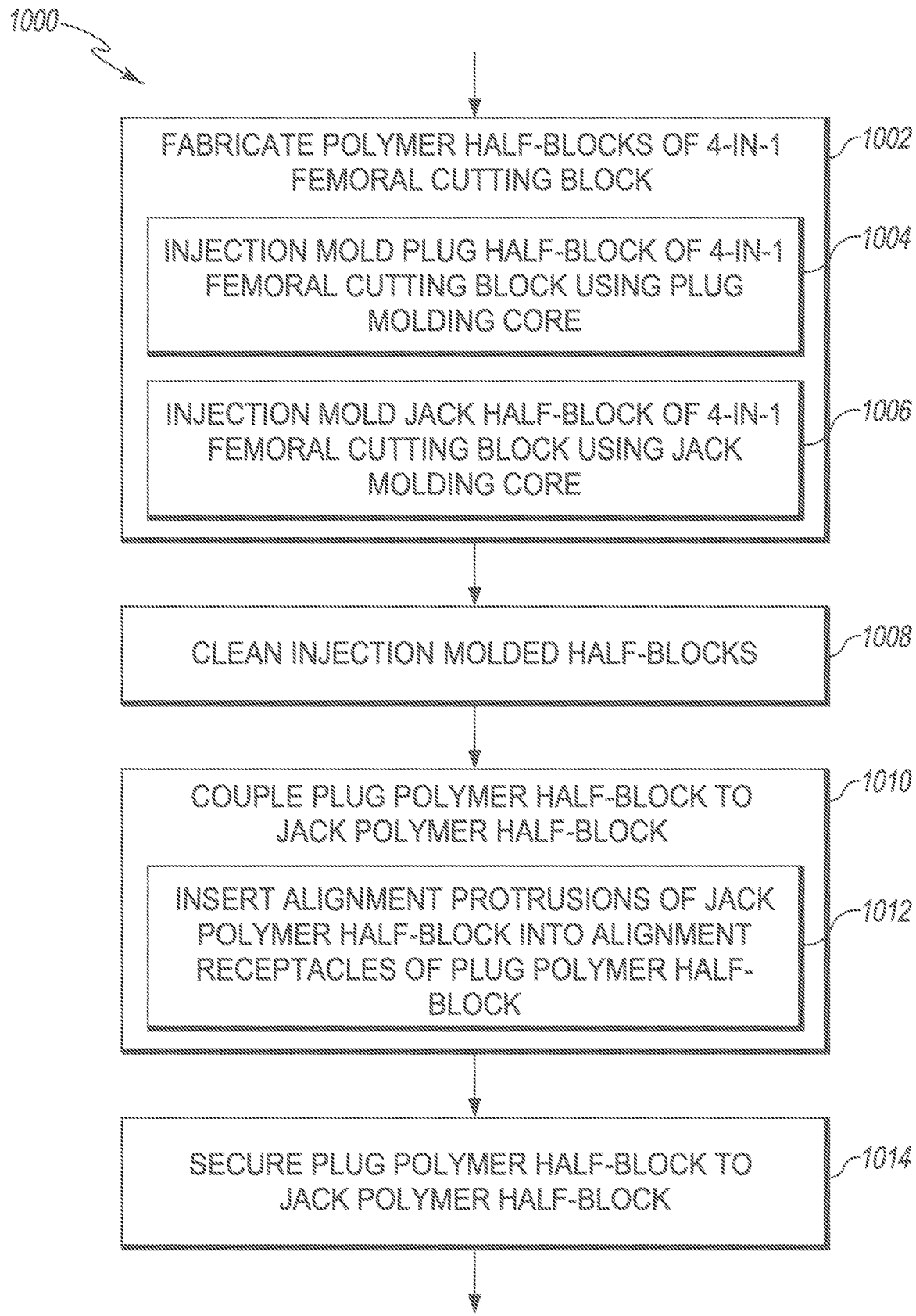
FIG. 10 is a simplified flow diagram of a method for fabricating the all-polymer 4-in-1 cutting block of FIG. 1.
Figure 11:
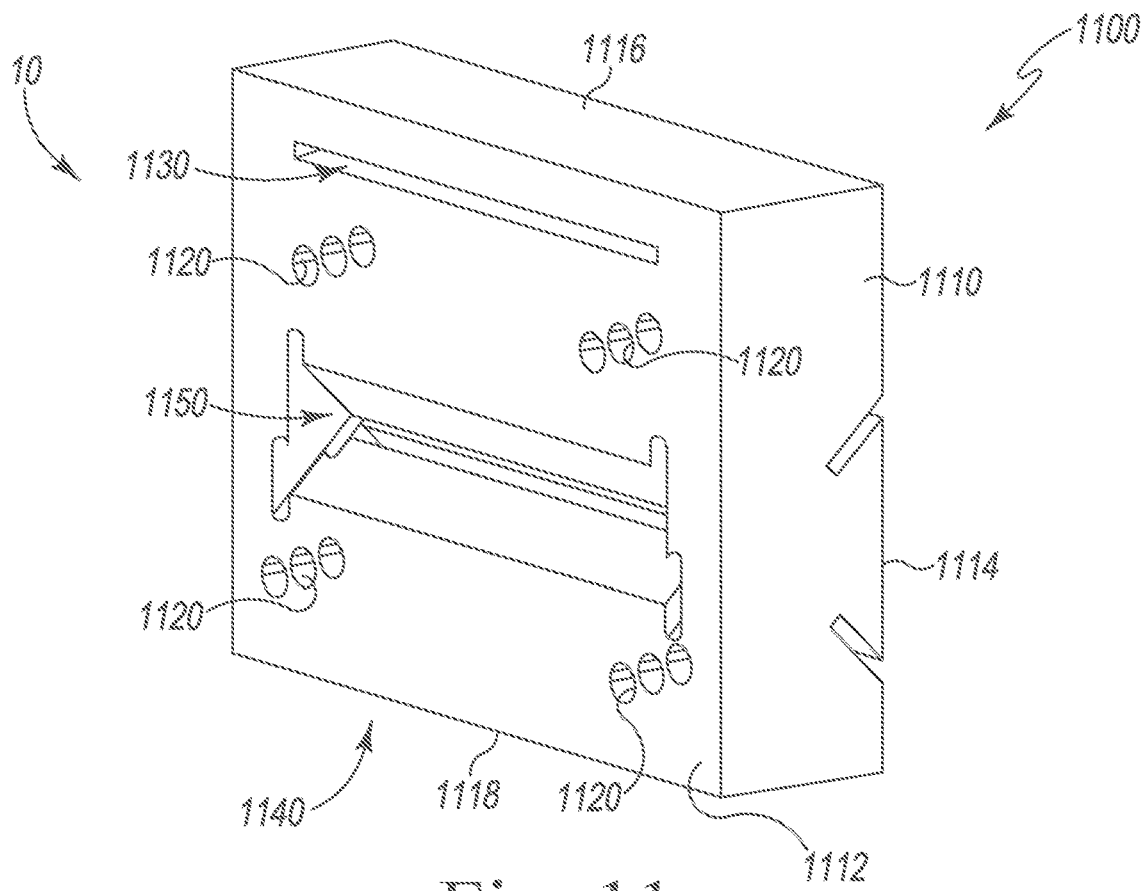
FIG. 11 is a perspective, elevation view of another embodiment of an all-polymer 4-in-1 cutting block showing an outer surface of the all-polymer 4-in-1 cutting block.
Figure 12:
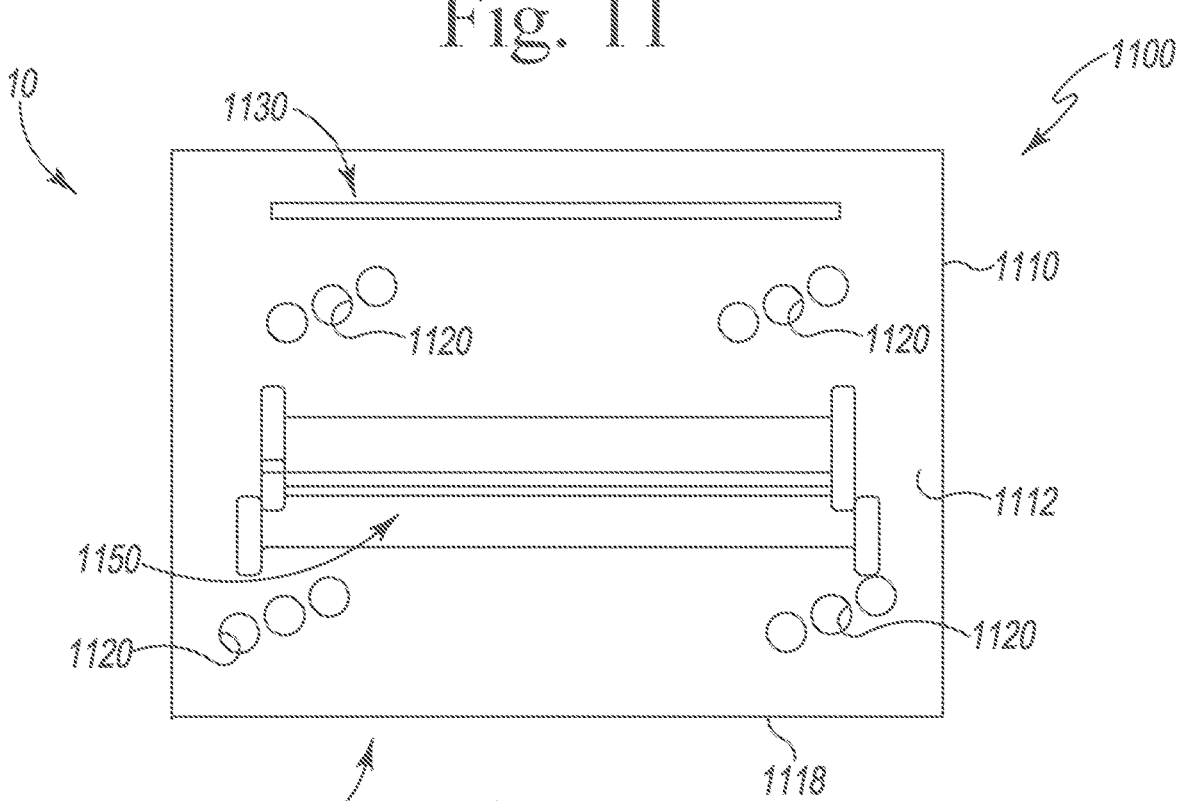
FIG. 12 is an elevation view of the all-polymer 4-in-1 cutting block of FIG. 11 showing the outer surface.
Figure 13:
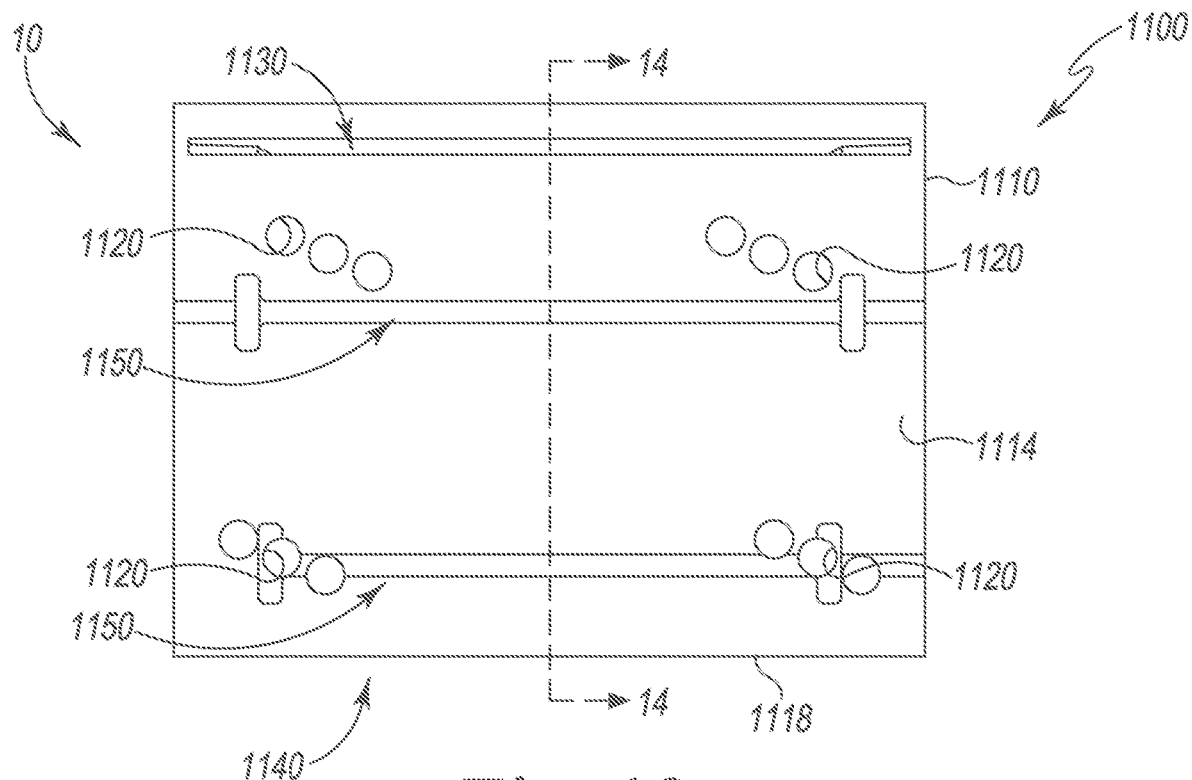
FIG. 13 is an elevation view of the all-polymer 4-in-1 cutting block of FIG. 11 showing the bone-engaging surface.

Referring now to FIG. 10, a method 1000 may be used to fabricate the all-polymer 4-in-1 cutting block 100. The method 1000 begins with block 1002 in which each of the plug polymer half-block 102 and the jack polymer half-block 202 are fabricated. For example, in block 1004, the plug polymer half-block 102 may be injection molded using a plug molding core 900 as described above. Similarly, in block 1006, the jack polymer half-block 202 may be injection molded using a jack molding core 900 as described above. The particular injection molding process used (e.g., the temperature and length of the molding process) may depend on various factors including, for example, the particular type of polymer used.

After the polymer half-blocks 102, 202 have been formed, the polymer half-block 102, 202 are cleaned in block 1008. The cleaning process removes any extraneous polymer pieces from the polymer half-blocks 102, 202. Additionally, fine detailing of the polymer half-blocks 102, 202 may be performed in block 1008. For example, the various cutting slots 130, 230, 140, 240, 150, 250 may be cleaned or further machined to ensure a cleaned and planar cutting guide.

Subsequently, in block 1010, the plug polymer half-block 102 and the jack polymer half-block 202 are coupled together. To do so, in block 1012, the alignment protrusions 260 of the jack polymer half-block 202 are received in the alignment receptacles 160 of the plug polymer half-block 102 as discussed above. The polymer half-blocks 102, 202 may then be secured together in block 1014. For example, as discussed above, the polymer half-blocks 102, 202 may be secured to each other via use of the securing devices 700 as discussed above in regard to FIG. 7.

Referring now to FIGS. 11-23, in another illustrative embodiment, the orthopaedic surgical instrument 10 is embodied as an all-polymer 4-in-1 cutting block 1100. The illustrative all-polymer 4-in-1 cutting block 1100 includes a polymer body 1110 having an outer surface 1112 and a bone-engaging surface 1114 opposite the outer surface 1112. The polymer body 1110 also includes an anterior end 1116 and a posterior end 1118 opposite the anterior end 1116. Additionally, the polymer body 1110 includes a number of mounting apertures 1120 defined therethrough and configured to facilitate the attachment of the all-polymer 4-in-1 cutting block 1100 to a distal end of the patient's surgically-prepared femur using corresponding securing devices, such as bone screws.

Figure 14:
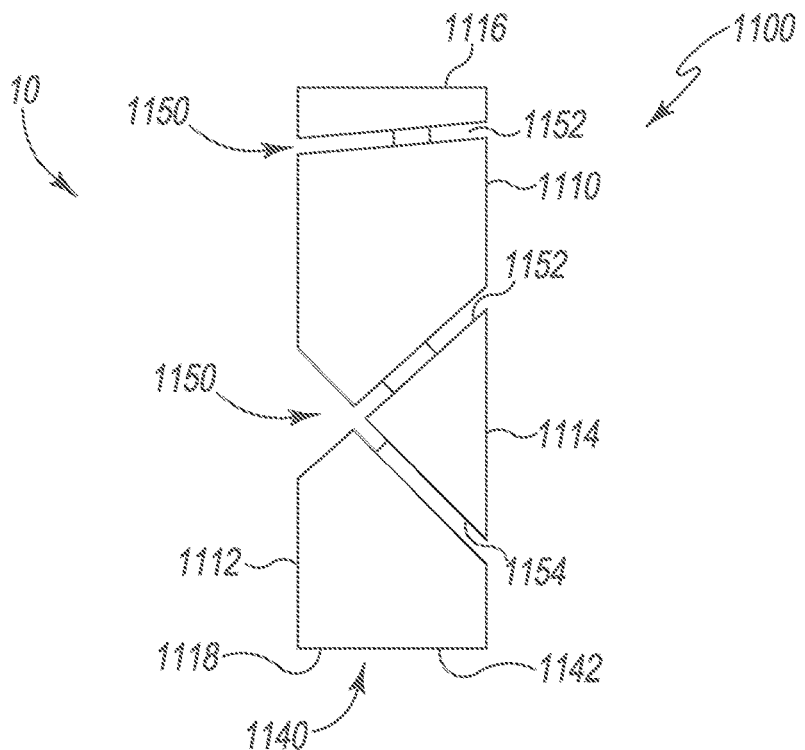
FIG. 14 is a cross-sectional view of the all-polymer 4-in-1 cutting block of FIG. 11 taken generally along line 14-14 of FIG. 13.
Figure 15:
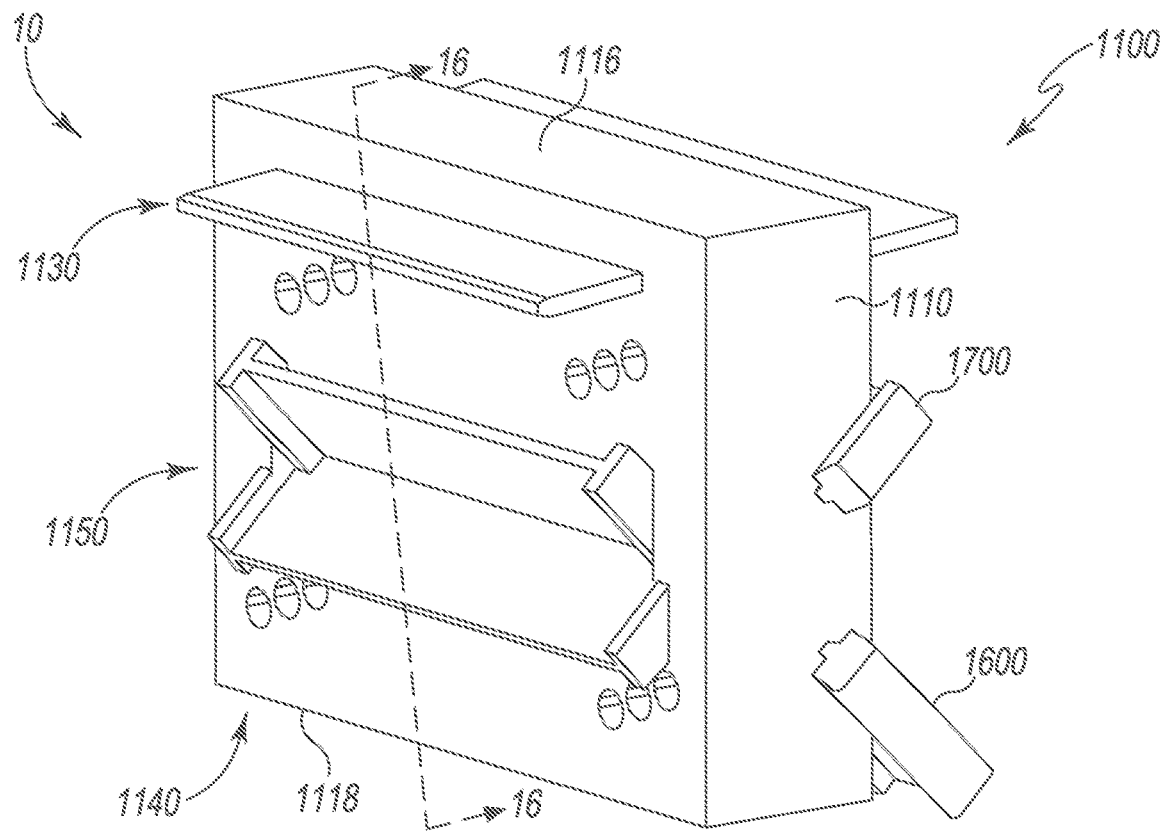
FIG. 15 is a perspective, elevation view of the all-polymer 4-in-1 cutting block of FIG. 11 having an anterior cutting guide core, an anterior chamfer cutting guide core, and a posterior chamfer cutting guide core inserted into a polymer body of the all-polymer 4-in-1 cutting block during an injection molding fabrication process.
Figure 16:
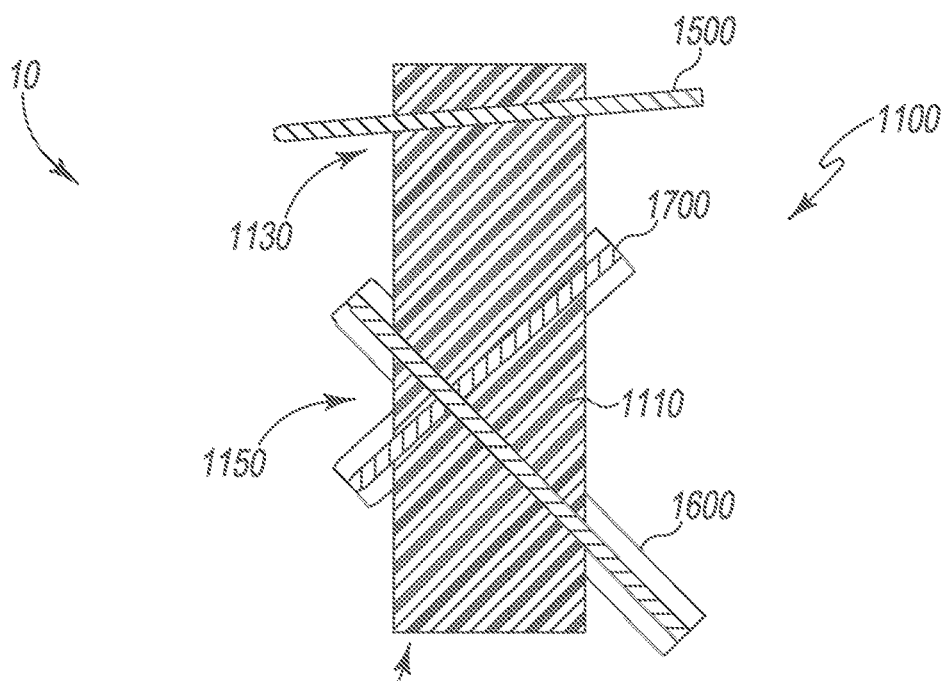
FIG. 16 is a cross-sectional view of the all-polymer 4-in-1 cutting block of FIG. 15 taken generally along line 15-15 of FIG. 15.

The polymer body 1110 of the all-polymer 4-in-1 cutting block 1100 also includes a polymer anterior cutting guide 1130, a polymer posterior cutting guide 1140, and a polymer chamfer cutting guide 1150. As best shown in FIG. 14, the anterior cutting guide 1130 is embodied as a captured cutting slot 1132 that extends from the outer surface 1112 to the bone-engaging surface 1114 of the polymer body 1110. The polymer posterior cutting guide 1140 is embodied as a posterior cutting surface 1142 that also extends from the outer surface 1112 to the bone-engaging surface 1114 of the polymer body 1110. The polymer chamfer cutting guide 1150 is formed from a captured anteriorly-angled cutting slot 1152 and a captured posteriorly-angled cutting slot 1154, which intersect each other and extend from the outer surface 1112 to the bone-engaging surface 1114 of the polymer body 1110.

As shown in FIGS. 15-23 and described in more detail below, each of the polymer anterior cutting guide 1130 and the polymer chamfer cutting guide 1150 is formed during an injection molding process using an anterior cutting guide core 1500, an anterior chamfer cutting guide core 1600, and a posterior chamfer cutting guide core 1700. Each of the cores 1500, 1600, 1700 are formed from a metallic material, such as steel or a titanium alloy, having a melting point high enough to withstand the temperatures of the injection molding process.

Figure 17:
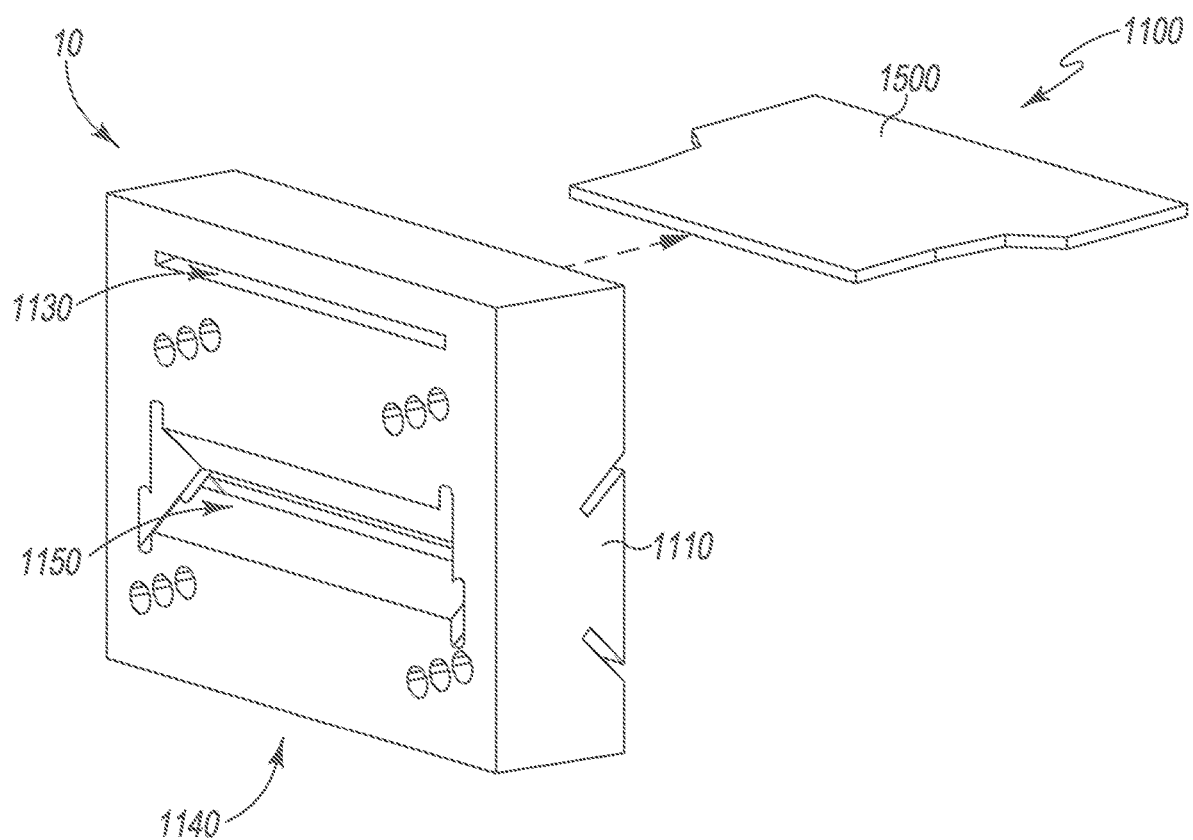
FIG. 17 is a perspective, elevation view of the all-polymer 4-in-1 cutting block of FIG. 11 showing the removal of the anterior cutting guide core subsequent to the injection molding fabrication process.
Figure 18:
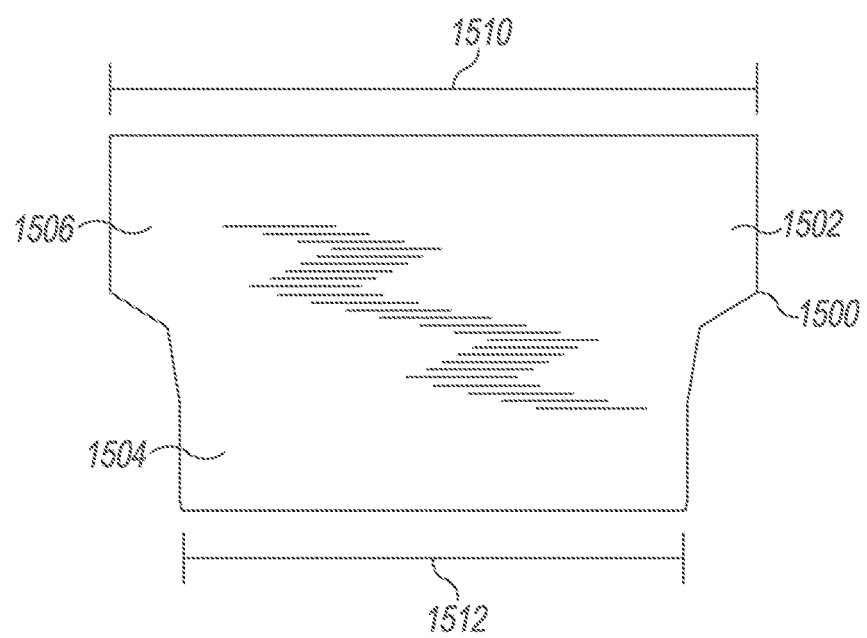
FIG. 18 is a top plan view of the anterior cutting guide core.

As shown in FIGS. 17 and 18, the anterior cutting guide core 1500 is used during the injection molding process to define the captured cutting slot 1132, which defines the polymer anterior cutting guide 1130. The anterior cutting guide core 1500 includes a planar body 1502 having an anterior cutting guide molding end 1504 and a handle end 1506 opposite the anterior cutting guide molding end 1504. The handle end 1506 may be used to properly position the anterior cutting guide core 1500, and the anterior cutting guide molding end 1504 is configured to form the captured cutting slot 1132 during the injection molding process. As shown in FIG. 18, the handle end 1506 has width 1510 that is greater than a width 1512 of the anterior cutting guide molding end 1504.

As shown in FIGS. 19-23, the anterior chamfer cutting guide core 1600 and the posterior chamfer cutting guide core 1700 are configured to couple to each other and used during the injection molding process to define the captured anteriorly-angled cutting slot 1152 and the captured posteriorly-angled cutting slot 1154, which cooperate to define the polymer chamfer cutting guide 1150.

Figure 20:
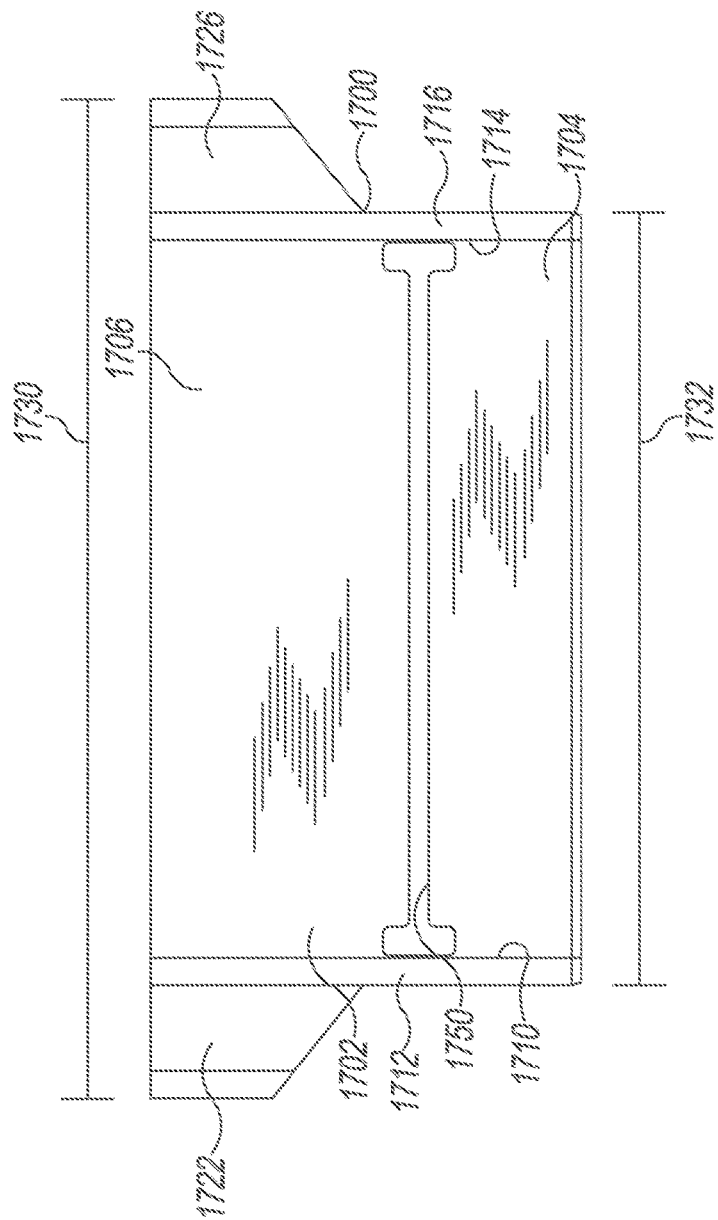
FIG. 20 is a top plan view of the posterior chamfer cutting guide core.
Figure 21:
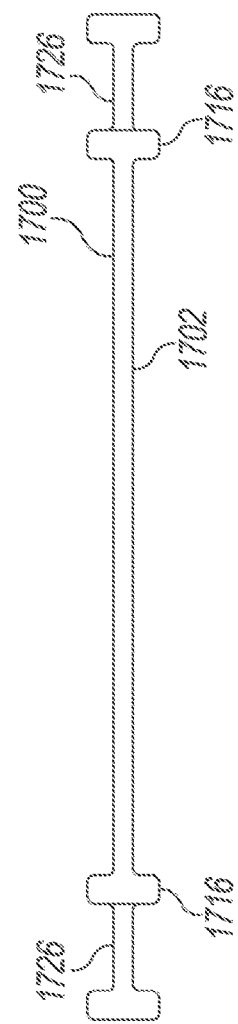
FIG. 21 is an end elevation view of the posterior chamfer cutting guide core of FIG. 20.

As shown best in FIG. 20, the illustrative posterior chamfer cutting guide core 1700 includes a planar body 1702 having a chamfer cutting guide molding end 1704 and a handle end 1706 opposite the chamfer cutting guide molding end 1704. Similar to the anterior cutting guide core 1500, the handle end 1706 of the posterior chamfer cutting guide core 1700 may be used to properly position the posterior chamfer cutting guide core 1700. The chamfer cutting guide molding end 1704 is configured to form the posteriorly-angled cutting slot 1154 during the injection molding process.

Figure 19:
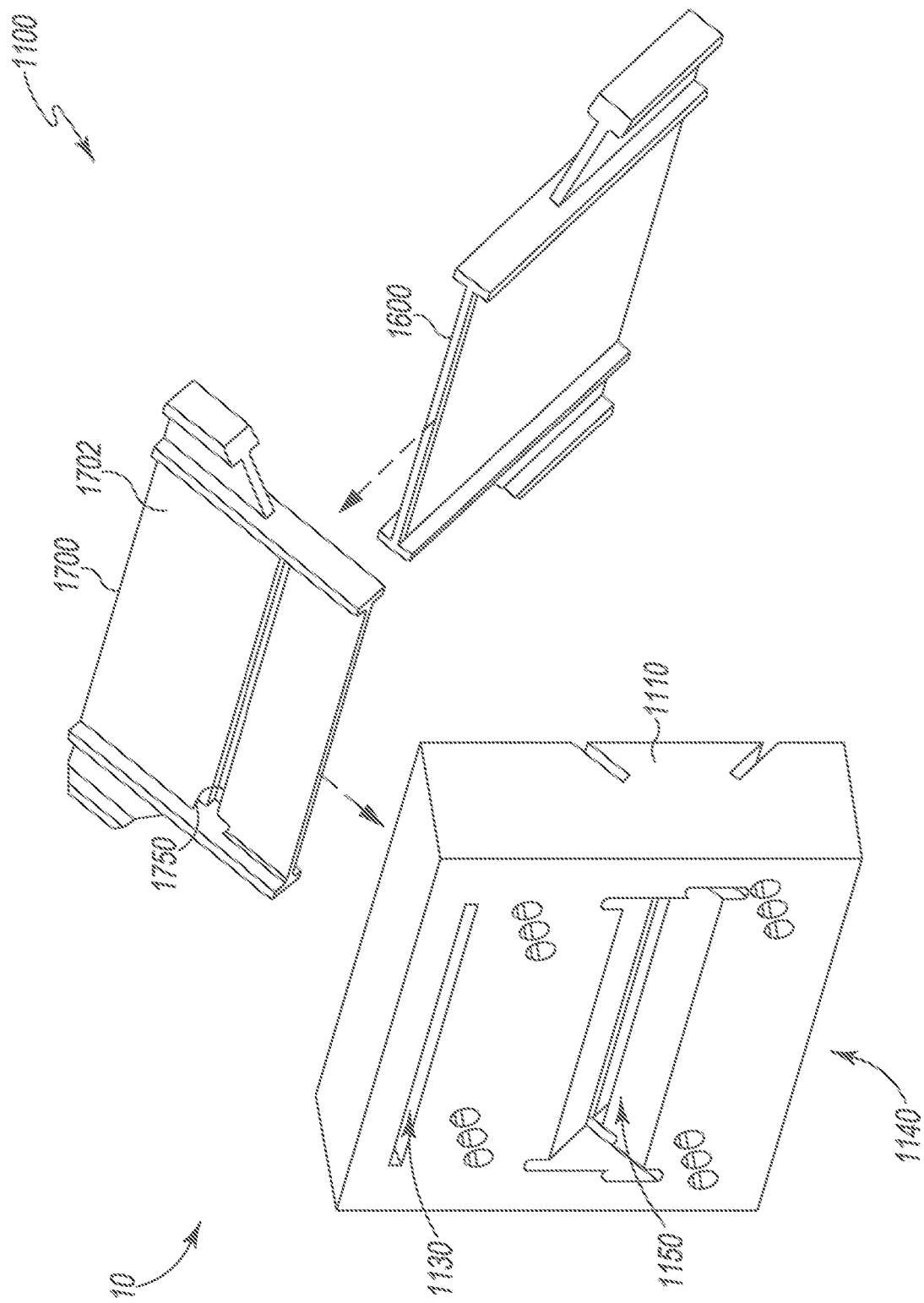
FIG. 19 is a perspective, elevation view of the all-polymer 4-in-1 cutting block of FIG. 11 showing the removal of the anterior and posterior chamfer cutting guide cores subsequent to the injection molding fabrication process.

The planar body 1702 of the posterior chamfer cutting guide core 1700 also includes a medial side 1710 and a lateral side 1714 opposite the medial side 1710. A medial side-rail 1712 is attached to the medial side 1710 of the planar body 1702, and a lateral side-rail 1716 is attached to the lateral side 1714. The side-rails 1712, 1716 improve the rigidity of the planar body 1702, which may allow the planar body 1702 to have a smaller thickness than otherwise would be obtainable without the additional support provided by the side-rails 1712, 1716. The posterior chamfer cutting guide core 1700 also includes a medial stop flange 1722 and a lateral stop flange 1726. The medial stop flange 1722 is attached to the medial side-rail 1712 and extends outwardly therefrom, and the lateral stop flange 1726 is attached to the lateral side-rail 1716 and extends outwardly therefrom. As such, the stop flanges 1722, 1726 define a width 1730 of the handle end 1706 that is greater than a width 1732 of the chamfer cutting guide molding end 1704 as shown in FIG. 20. The planar body 1702 also includes a slot 1750 defined therethrough. As shown in FIG. 19 and described in more detail below, the slot 1750 is shaped and sized so as to allow the anterior chamfer cutting guide core 1600 to be inserted through the planar body 1702 of the posterior chamfer cutting guide core 1700.

The anterior chamfer cutting guide core 1600 is substantially similar to the posterior chamfer cutting guide core 1700. For example, as shown best in FIG. 22, the illustrative anterior chamfer cutting guide core 1600 includes a planar body 1602 having a chamfer cutting guide molding end 1604 and a handle end 1606 opposite the chamfer cutting guide molding end 1604. Again, similar to the anterior cutting guide core 1500, the handle end 1606 of the anterior chamfer cutting guide core 1600 may be used to properly position the anterior chamfer cutting guide core 1600. The chamfer cutting guide molding end 1604 is configured to form the anteriorly-angled cutting slot 1152 during the injection molding process.

The planar body 1602 of the anterior chamfer cutting guide core 1600 also includes a medial side 1610 and a lateral side 1614 opposite the medial side 1610. A medial side-rail 1612 is attached to the medial side 1610 of the planar body 1602, and a lateral side-rail 1616 is attached to the lateral side 1614. The side-rails 1612, 1616 improve the rigidity of the planar body 1602, which may allow the planar body 1602 to have a smaller thickness than otherwise would be obtainable without the additional support provided by the side-rails 1612, 1616 as discussed above. The anterior chamfer cutting guide core 1600 also includes a medial stop flange 1622 and a lateral stop flange 1626. The medial stop flange 1622 is attached to the medial side-rail 1612 and extends outwardly therefrom, and the lateral stop flange 1626 is attached to the lateral side-rail 1616 and extends outwardly therefrom. As such, the stop flanges 1622, 1626 define a width 1630 of the handle end 1606 that is greater than a width 1632 of the chamfer cutting guide molding end 1604 as shown in FIG. 22.

Because the anterior chamfer cutting guide core 1600 is configured to be inserted into the slot 1750 of the posterior chamfer cutting guide core 1700, the illustrative planar body 1602 of the anterior chamfer cutting guide core 1600 is devoid of any slot similar to the slot 1750. However, in other embodiments, the posterior chamfer cutting guide core 1700 may be configured to be inserted into the anterior chamfer cutting guide core 1600 and, in such embodiments, the anterior chamfer cutting guide core 1600 may include a slot similar to slot 1750. In such embodiments, the posterior chamfer cutting guide core 1700 may or may not include the slot 1750. To facilitate the coupling of the chamfer cutting guide cores 1600, 1700, it should be appreciated that the width 1632 of the chamfer cutting guide molding end 1604 of the anterior chamfer cutting guide core 1600 is similar to the width of the slot 1750 and less than the width 1732 of the chamfer cutting guide molding end 1704 of the posterior chamfer cutting guide core 1700.

Figure 24:
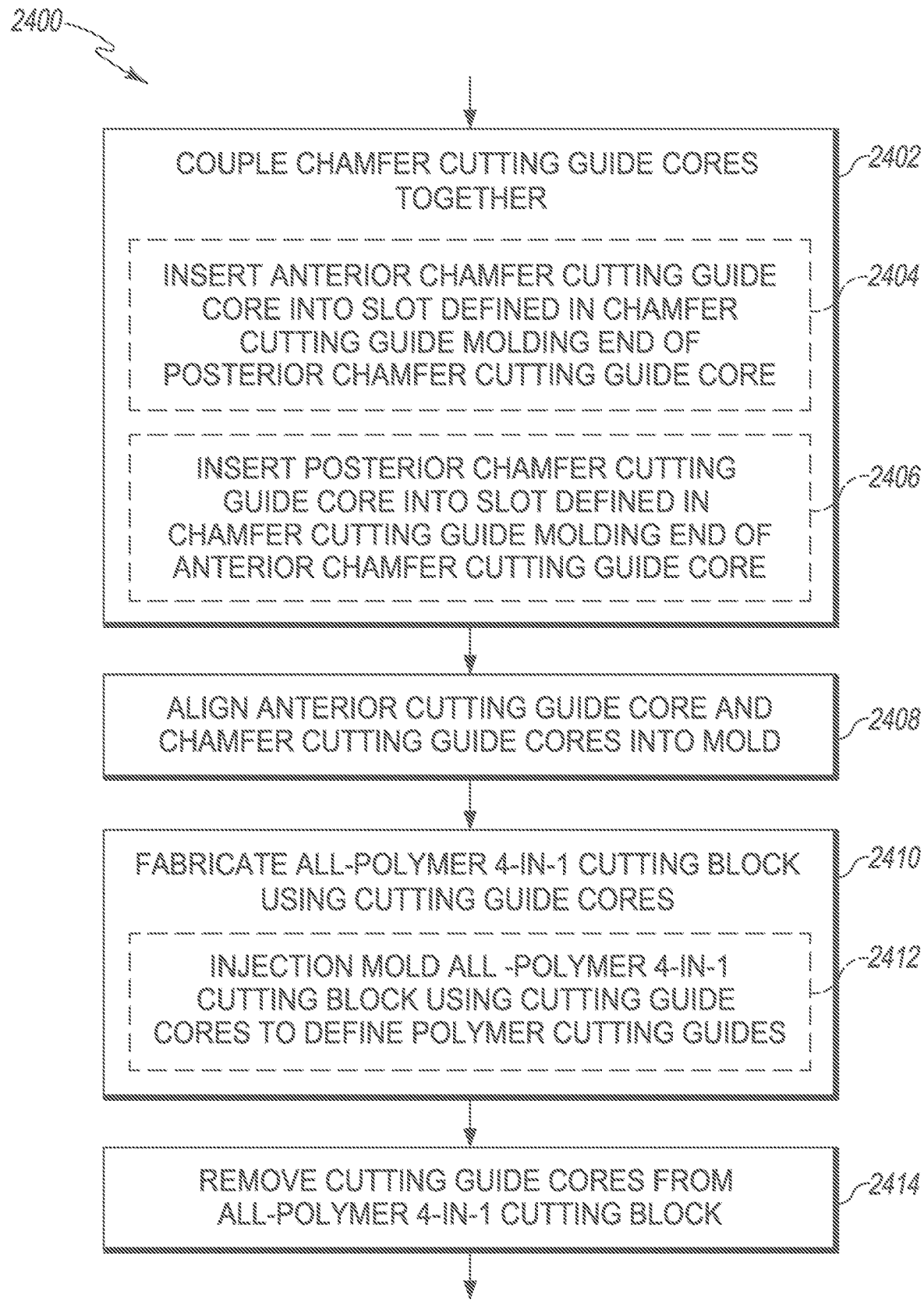
FIG. 24 is a simplified flow diagram of a method for fabricating the all-polymer 4-in-1 cutting block of FIG. 11.
Figure 25:
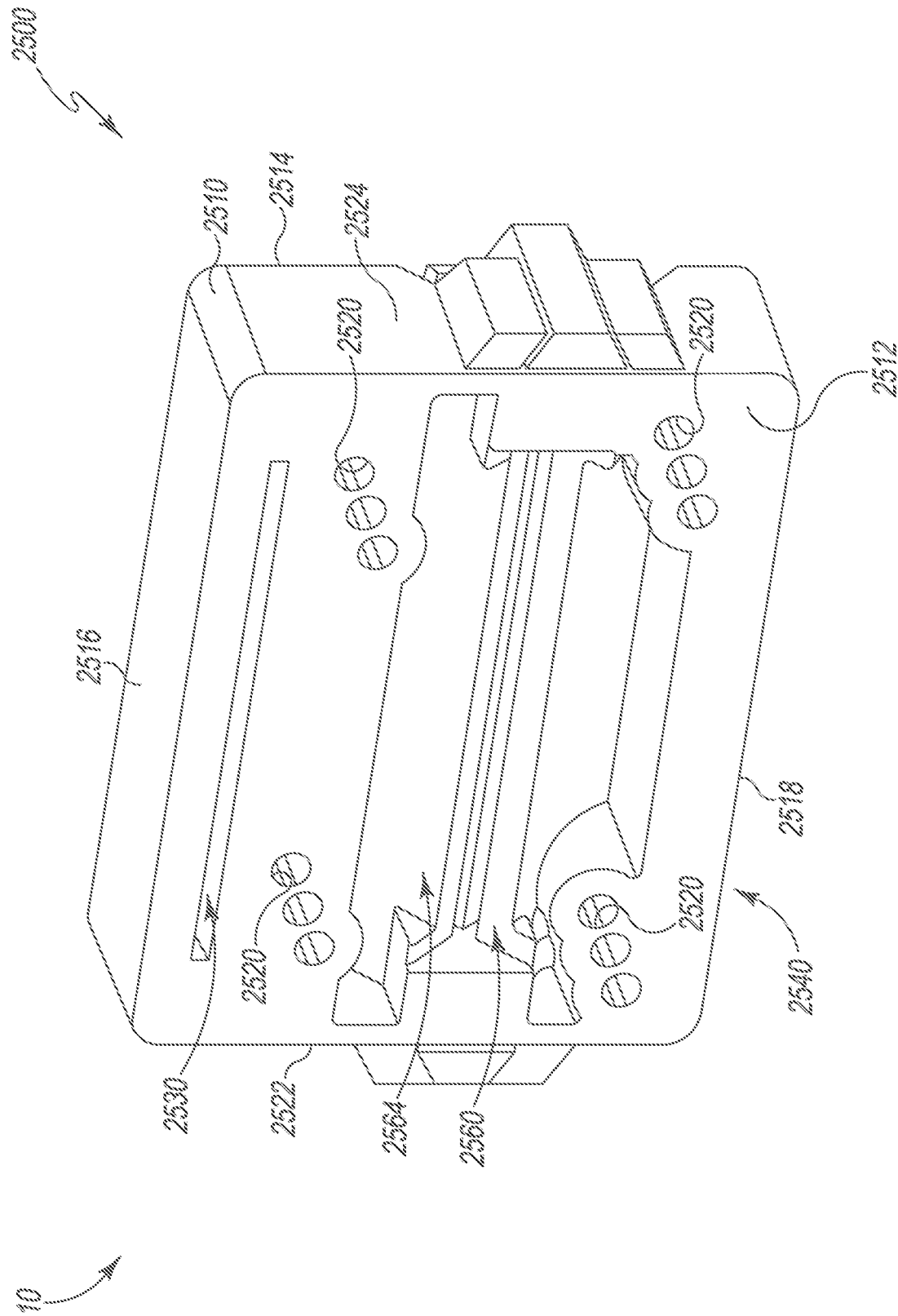
FIG. 25 is a perspective, elevation view of another embodiment of an all-polymer 4-in-1 cutting block showing an outer surface of the all-polymer 4-in-1 cutting block.

Referring now to FIG. 24, in use, a method 2400 may be executed for fabricating the all-polymer 4-in-1 cutting block 1100. The method 2400 begins with block 2402 in which the anterior chamfer cutting guide core 1600 and the posterior chamfer cutting guide core 1700 are coupled together. To do so and depending on the particular embodiment, the anterior chamfer cutting guide core 1600 may be inserted into the slot 1750 of the planar body 1702 of the posterior chamfer cutting guide core 1700 in block 2404. Alternatively, in other embodiments, the posterior chamfer cutting guide core 1700 may be inserted into a slot defined in the planar body 1602 of the anterior chamfer cutting guide core 1600 in block 2406.

Regardless, after the chamfer cutting guide cores 1600, 1700 have been coupled to each other, the anterior cutting guide core 1500 and the chamfer cutting guide cores 1600, 1700 are positioned and aligned into the injection mold in block 2408. In block 2410, the all-polymer 4-in-1 cutting block 1100 is formed via an injection modeling process and using the cutting guide cores 1500, 1600, 1700. In doing so, in block 2412, the anterior cutting guide core 1500 forms the polymer anterior cutting guide 1130 and the chamfer cutting guide cores 1600, 1700 cooperate to define the polymer chamfer cutting guide 1150.

After the all-polymer 4-in-1 cutting block 1100 has been fabricated in block 2410, the method 2400 advances to block 2414. In block 2414, the cutting guide cores 1500, 1600, 1700 are removed from the all-polymer 4-in-1 cutting block 1100. To do so, the anterior chamfer cutting guide core 1600 may be initially removed from the all-polymer 4-in-1 cutting block 1100 by sliding the anterior chamfer cutting guide core 1600 through the slot 1750 of the planar body 1702 of the posterior chamfer cutting guide core 1700 and from the all-polymer 4-in-1 cutting block 1100. After the anterior chamfer cutting guide core 1600 has been so removed, the posterior chamfer cutting guide core 1700 may be subsequently removed from the all-polymer 4-in-1 cutting block 1100.

Referring now to FIGS. 25-33, in another illustrative embodiment, the orthopaedic surgical instrument 10 is embodied as an all-polymer 4-in-1 cutting block 2500. The illustrative all-polymer 4-in-1 cutting block 2500 includes a polymer body 2510 and a polymer chamfer cutting guide insert 2570 configured to be coupled to the polymer body 2510 as discussed in more detail below. The polymer body 2510 includes an outer surface 2512 and a bone-engaging surface 2514 opposite the outer surface 2512. The polymer body 2510 also includes an anterior end 2516, a posterior end 2518 opposite the anterior end 2516, a medial side 2522, and a lateral side 2524 opposite the medial side 2522. Additionally, the polymer body 2510 includes a number of mounting apertures 2520 defined therethrough and configured to facilitate the attachment of the all-polymer 4-in-1 cutting block 2500 to a distal end of the patient's surgically-prepared femur using corresponding securing devices, such as bone screws.

Figure 33:
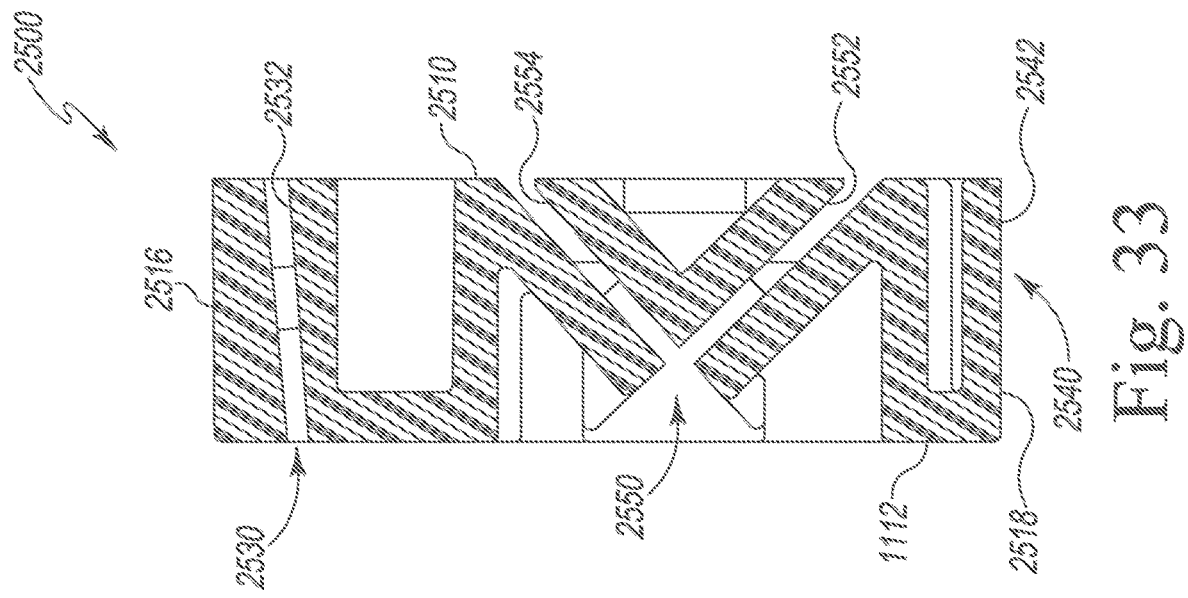
FIG. 33 is a cross-sectional view of the all-polymer 4-in-1 cutting block of FIG. 26 taken generally along line 33-33 of FIG. 26.
Figure 30:
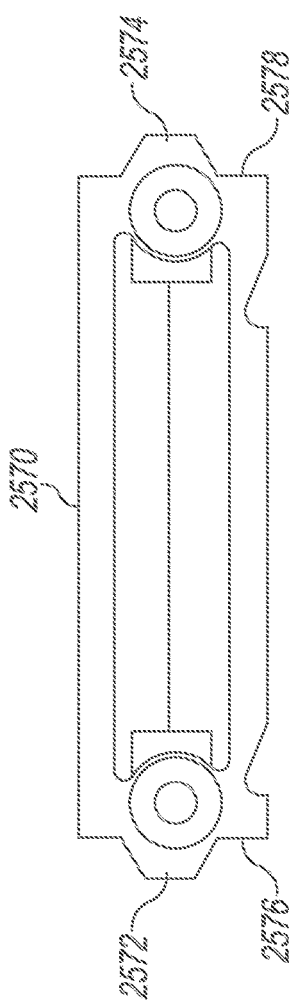
FIG. 30 is an elevation view of the polymer chamfer cutting guide insert of FIG. 27 showing an outer side of the polymer chamfer cutting guide.
Figure 31:
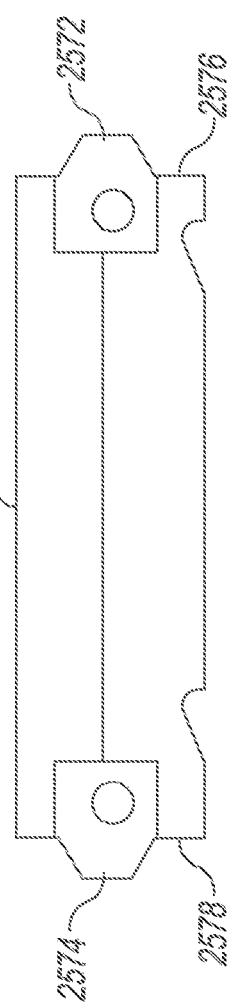
FIG. 31 is an elevation view of the polymer chamfer cutting guide insert of FIG. 27 showing an inner side of the polymer chamfer cutting guide.
Figure 32:
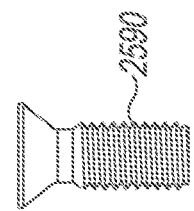
FIG. 32 is an elevation view of a securing device that may be used to secure the polymer chamfer cutting guide to the polymer body of the all-polymer 4-in-1 cutting block of FIG. 26.

The polymer body 2510 of the all-polymer 4-in-1 cutting block 2500 also includes a polymer anterior cutting guide 2530 and a polymer posterior cutting guide 2540. As best shown in FIG. 33, the anterior cutting guide 2530 is embodied as a captured cutting slot 2532 that extends from the outer surface 2512 to the bone-engaging surface 2514 of the polymer body 2510. The polymer posterior cutting guide 2540 is embodied as a posterior cutting surface 2542 that also extends from the outer surface 2512 to the bone-engaging surface 2514 of the polymer body 2510.

Figure 27:
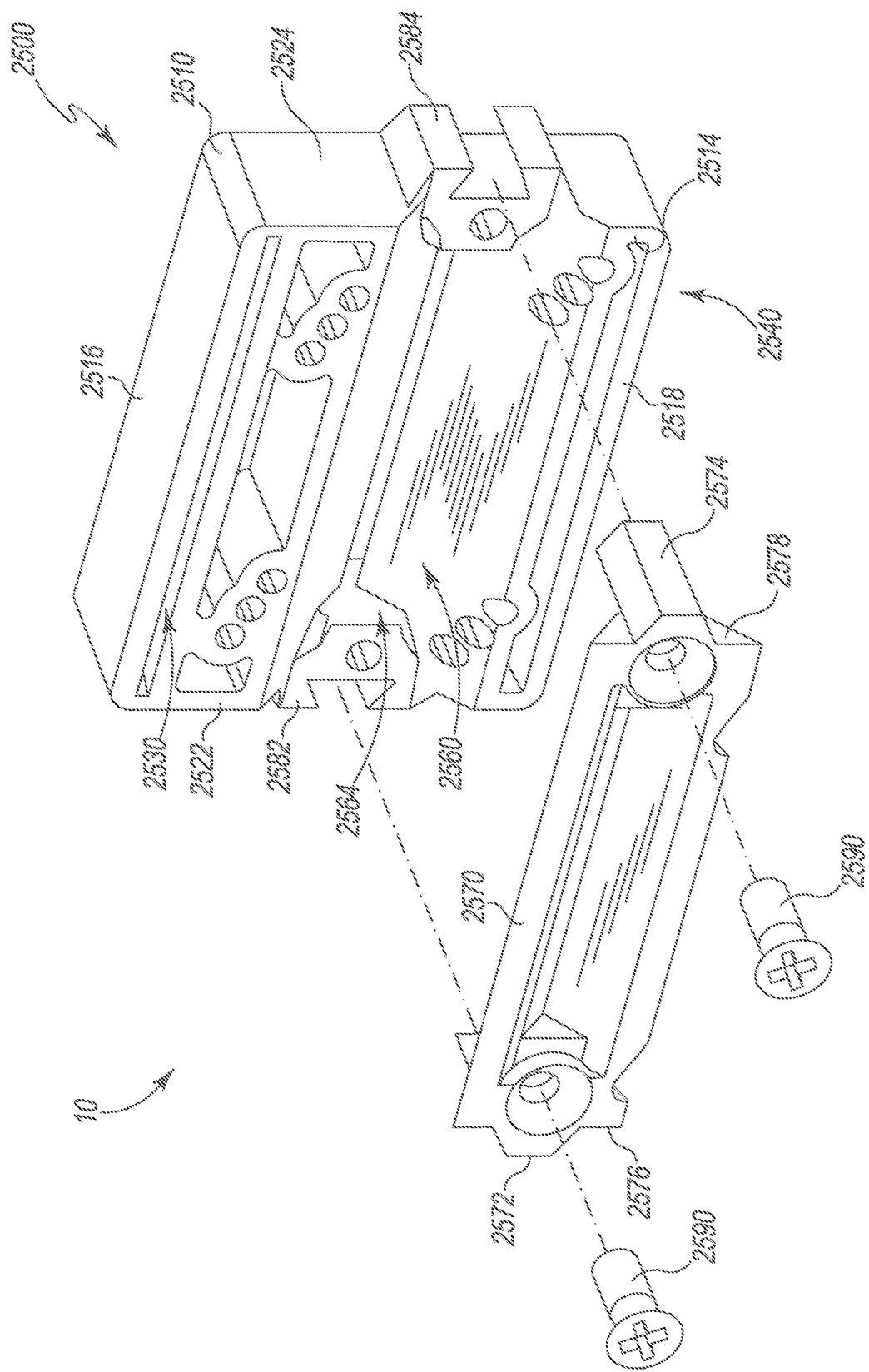
FIG. 27 is an exploded, perspective view of the all-polymer 4-in-1 cutting block of FIG. 26 showing a polymer chamfer cutting guide insert removed from a polymer body of the all-polymer 4-in-1 cutting block.
Figure 28:
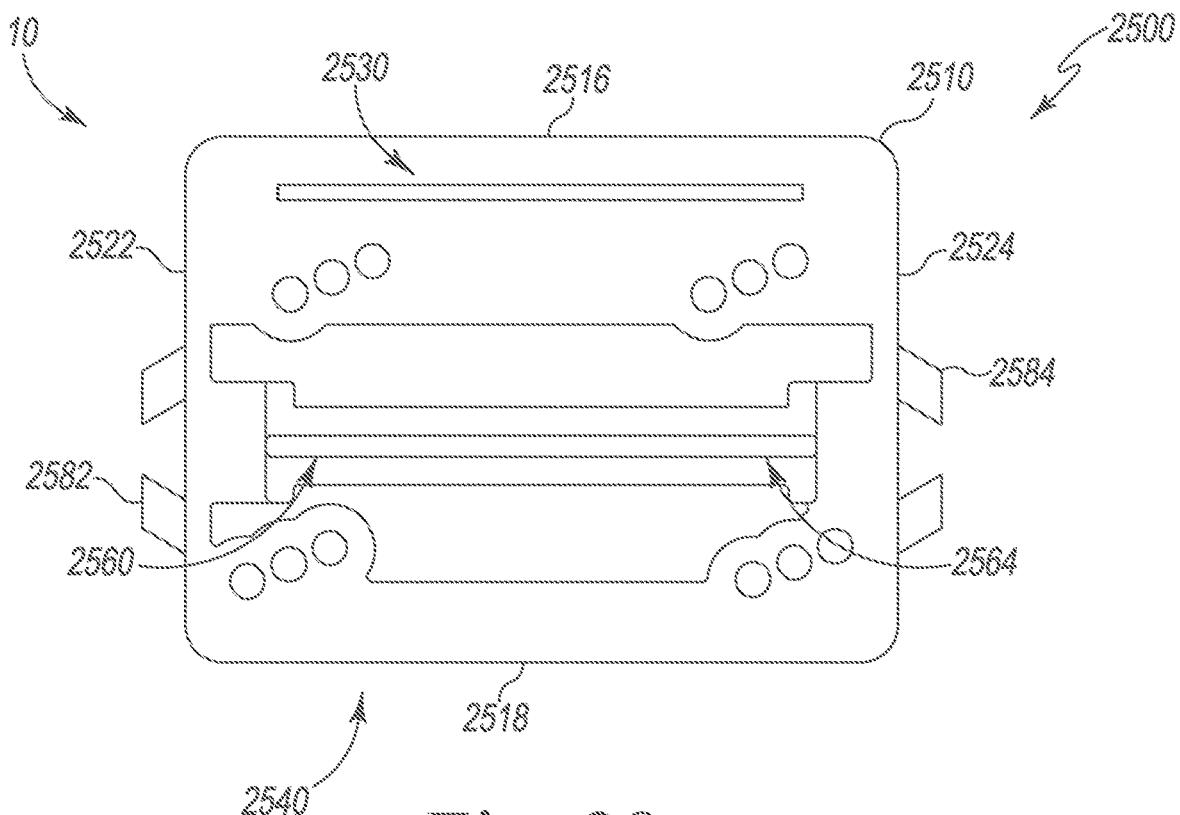
FIG. 28 is an elevation view of the all-polymer 4-in-1 cutting block of FIG. 26 with the polymer chamfer cutting guide insert removed from the polymer body and showing the outer surface of the polymer body.
Figure 29:
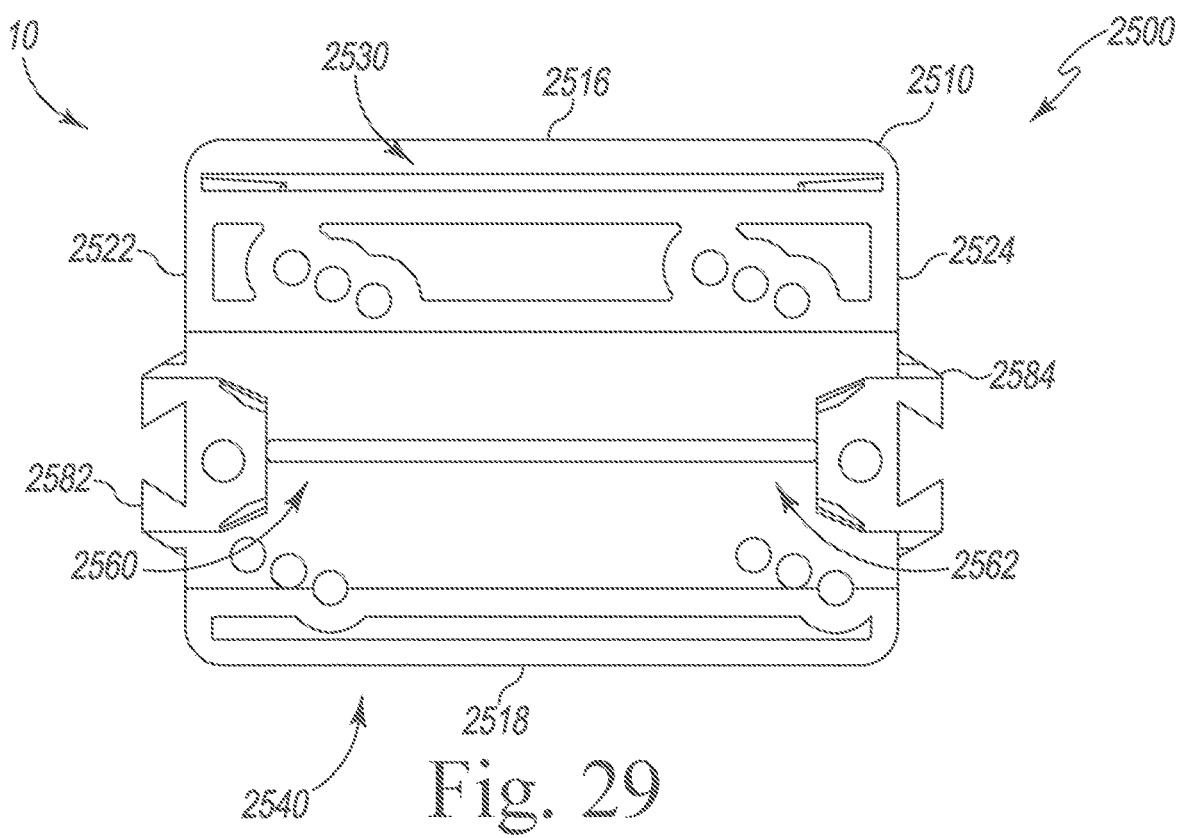
FIG. 29 is an elevation view of the all-polymer 4-in-1 cutting block of FIG. 26 with the polymer chamfer cutting guide insert removed from the polymer body and showing the bone-engaging surface of the polymer body.

The polymer body 2510 also includes a chamfer cutting guide recess 2560 positioned between the polymer anterior cutting guide 2530 and the polymer posterior cutting guide 2540. The chamfer cutting guide recess 2560 is embodied as an elongated recess that extends from the outer surface 2512 to the bone-engaging surface 2514 of the polymer body 2510. In particular, the chamfer cutting guide recess 2560 includes an opening 2562 located on the outer surface 2512 and an opening 2564 located on the bone-engaging surface 2514 that is larger than the opening 2562. The opening 2564 of the chamfer cutting guide recess 2560 is shaped and sized to receive the polymer chamfer cutting guide insert 2570 as best shown in FIG. 27. When the polymer chamfer cutting guide insert 2570 is received in the chamfer cutting guide recess 2560, the polymer chamfer cutting guide insert 2570 and the polymer body 2510 cooperate to define a polymer chamfer cutting guide 2550. Illustratively, the polymer chamfer cutting guide insert 2570 and the opening 2564 each have a corresponding triangular cross-sectional shape that defines an anteriorly-angled cutting slot 2552 and posteriorly angled cutting slot 2554, which extend away from each other as shown best in FIG. 33.

Figure 26:
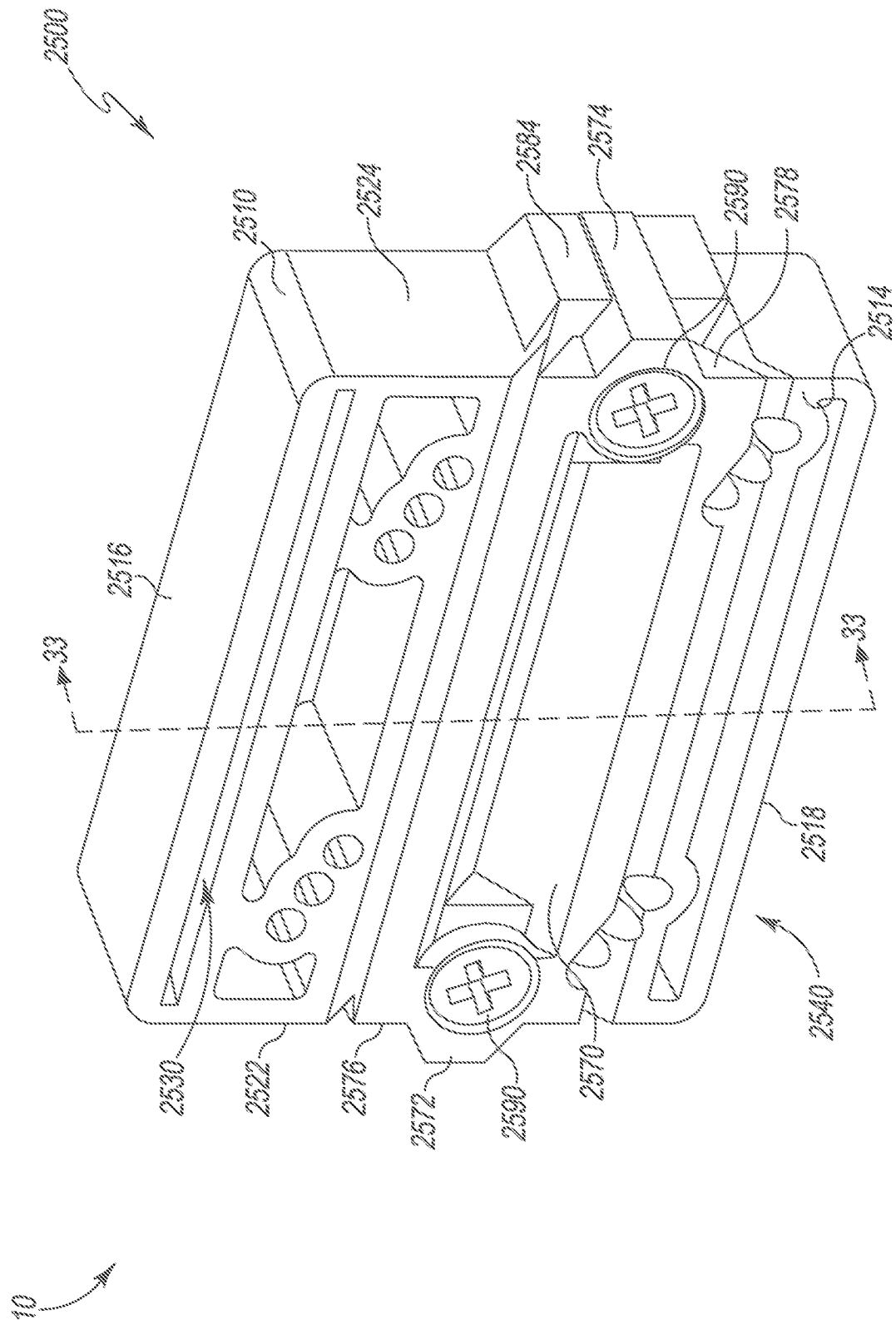
FIG. 26 is a perspective, elevation view of the all-polymer 4-in-1 cutting block of FIG. 26 showing a bone-engaging surface of the all-polymer 4-in-1 cutting block.

To facilitate the attachment of the polymer chamfer cutting guide insert 2570 to the polymer body 2510, the polymer body 2510 and the polymer chamfer cutting guide insert 2570 include features arranged to mate with each other. For example, the illustrative polymer body 2510 includes a medial guide track 2582 defined on the medial side 2522 and a lateral guide track 2584 defined on the lateral side 2524. And, the illustrative polymer chamfer cutting guide insert 2570 includes a medial guide arm 2572 extending from a medial side 2576 and a lateral guide arm 2574 extending from a lateral side 2578. As shown in FIGS. 26 and 27, the medial guide arm 2572 is configured to be received in the medial guide track 2582 and the lateral guide arm 2574 is configured to be received in the lateral guide track 2584 when the polymer chamfer cutting guide insert 2570 is coupled to the polymer body 2510. The polymer chamfer cutting guide insert 2570 may be secured to the polymer body 2510 via use of pair of securing devices 2590, which may be received through corresponding non-threaded apertures 2592 of the polymer chamfer cutting guide insert 2570 and threaded into threaded apertures 2594 of the polymer body 2510.

Figure 34:
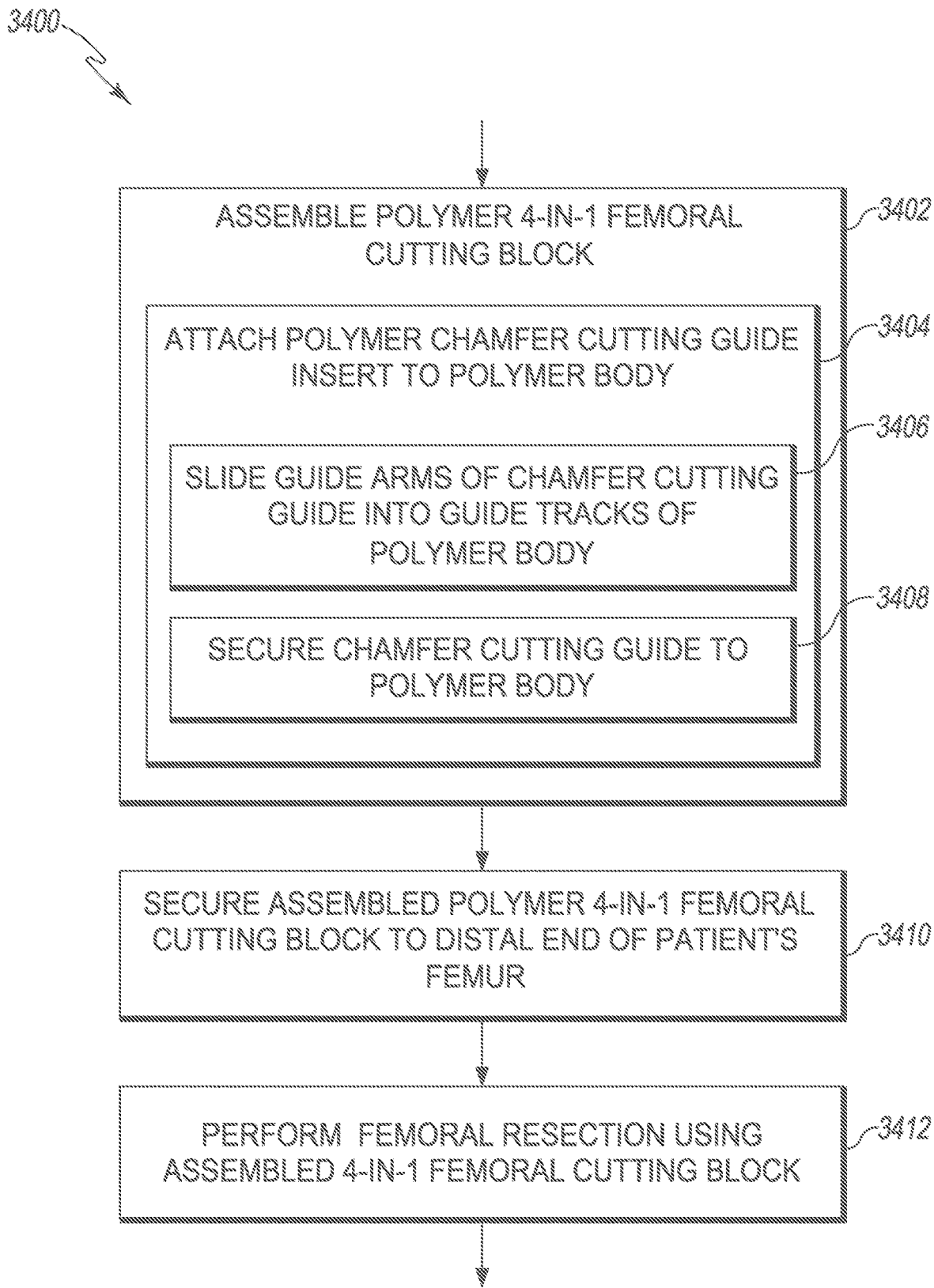
FIG. 34 is a simplified flow diagram of a method for performing an orthopaedic surgical procedure using the all-polymer 4-in-1 cutting block of FIG. 26.
Figure 35:
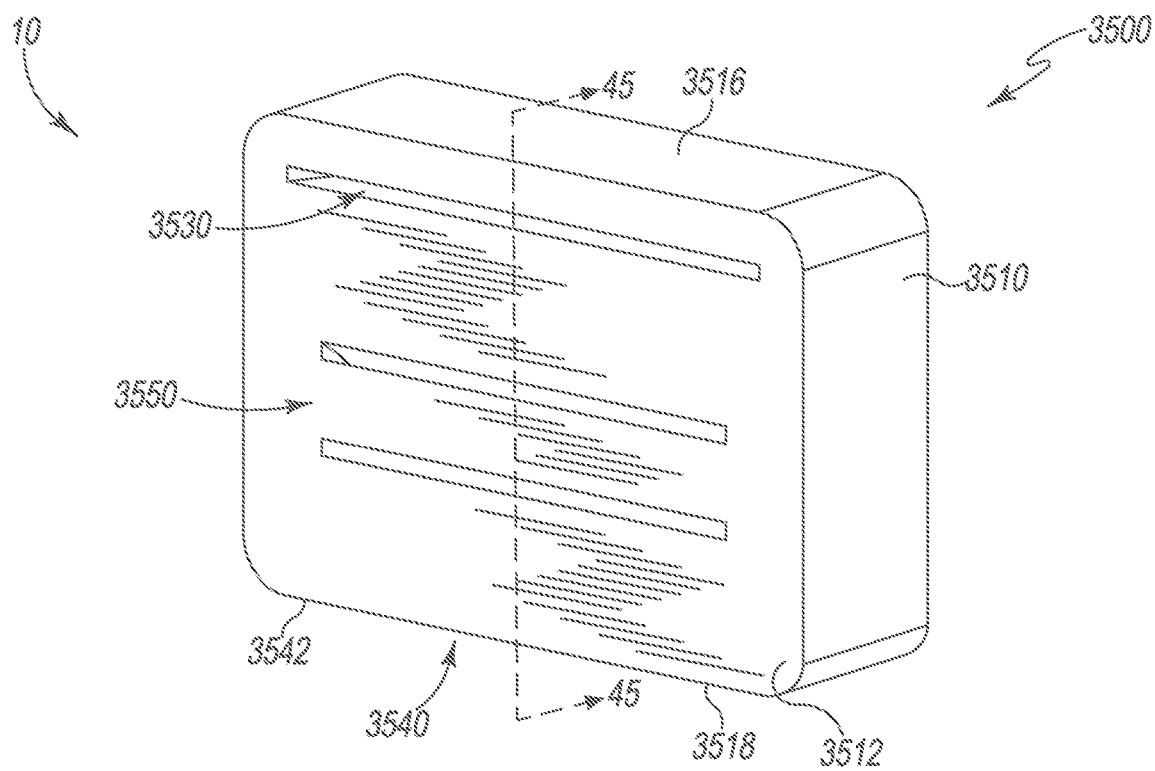
FIG. 35 is a perspective, elevation view of another embodiment of an all-polymer 4-in-1 cutting block showing an outer surface of the all-polymer 4-in-1 cutting block.
Figure 36:
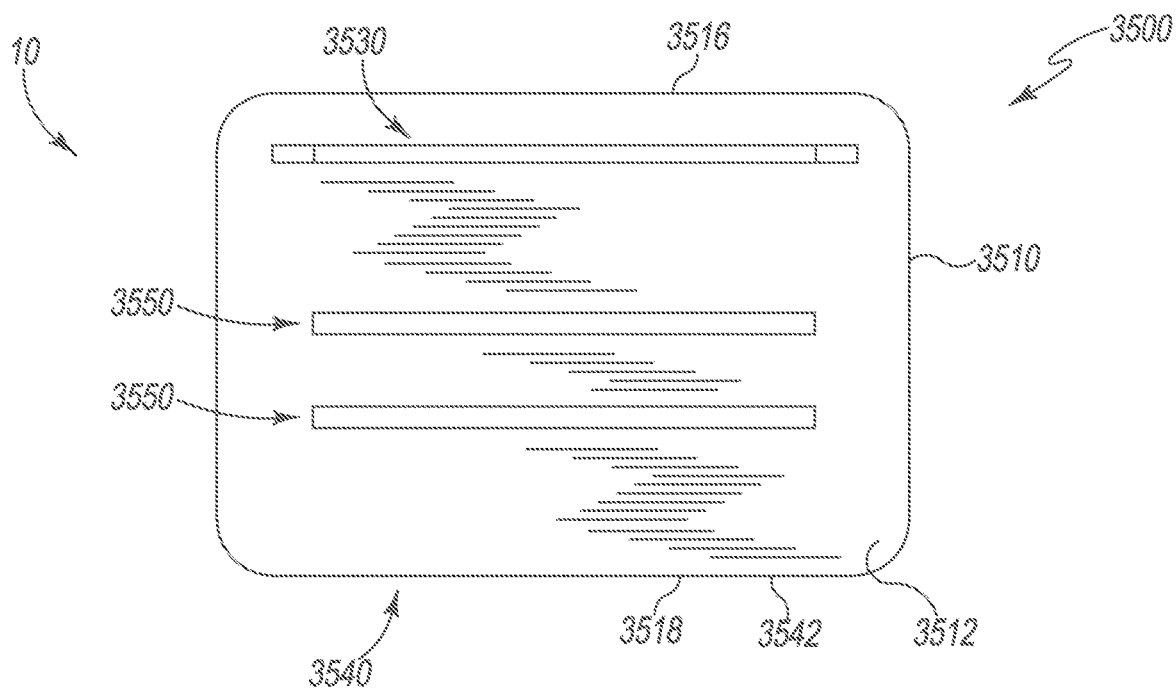
FIG. 36 is an elevation view of the all-polymer 4-in-1 cutting block of FIG. 36 showing the outer surface.
Figure 37:
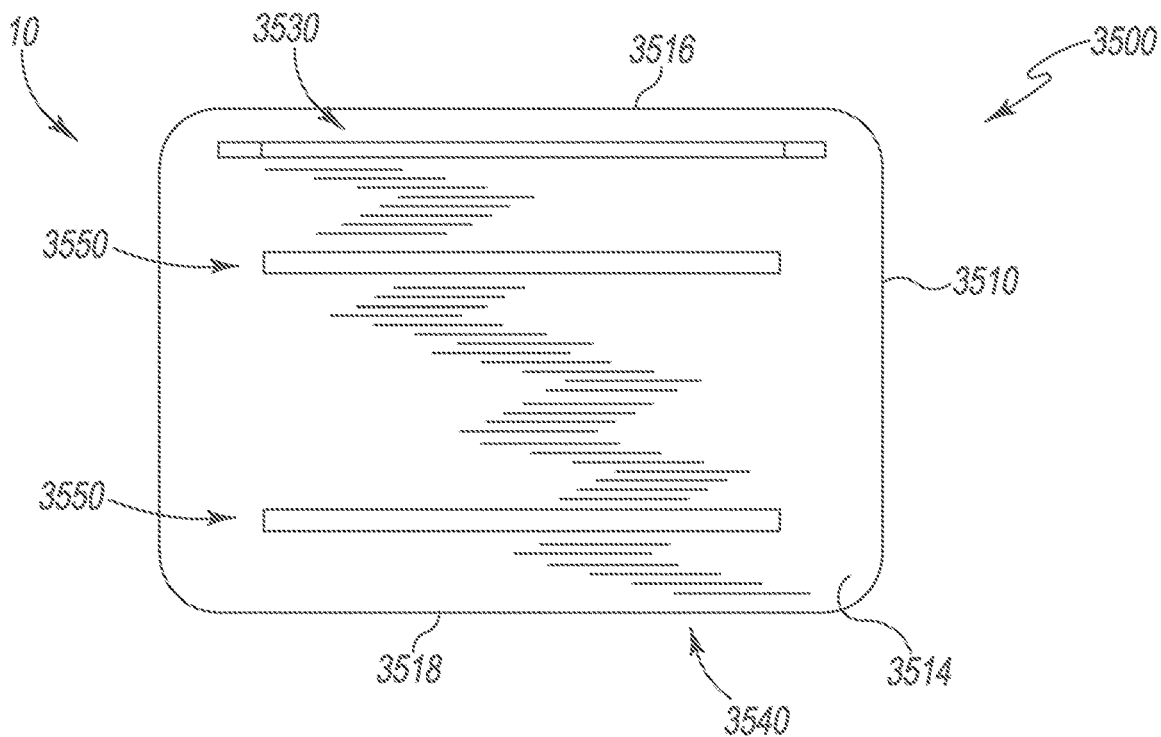
FIG. 37 is a perspective, elevation view of the all-polymer 4-in-1 cutting block of FIG. 35 showing a bone-engaging surface.
Figure 38:
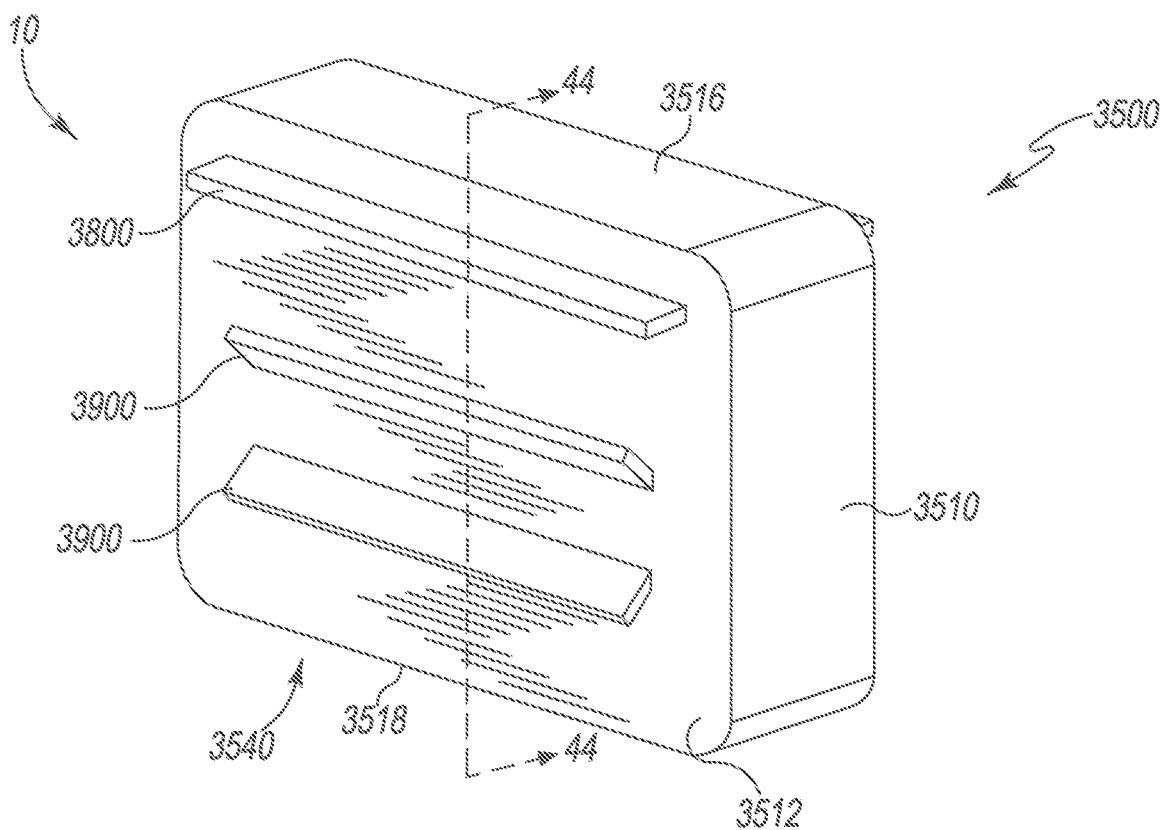
FIG. 38 is a perspective, elevation view of the all-polymer 4-in-1 cutting block of FIG. 35 including a sacrificial anterior cutting guide core and a sacrificial chamfer cutting guide core inserted therein prior to remove of the sacrificial cores.
Figure 39:
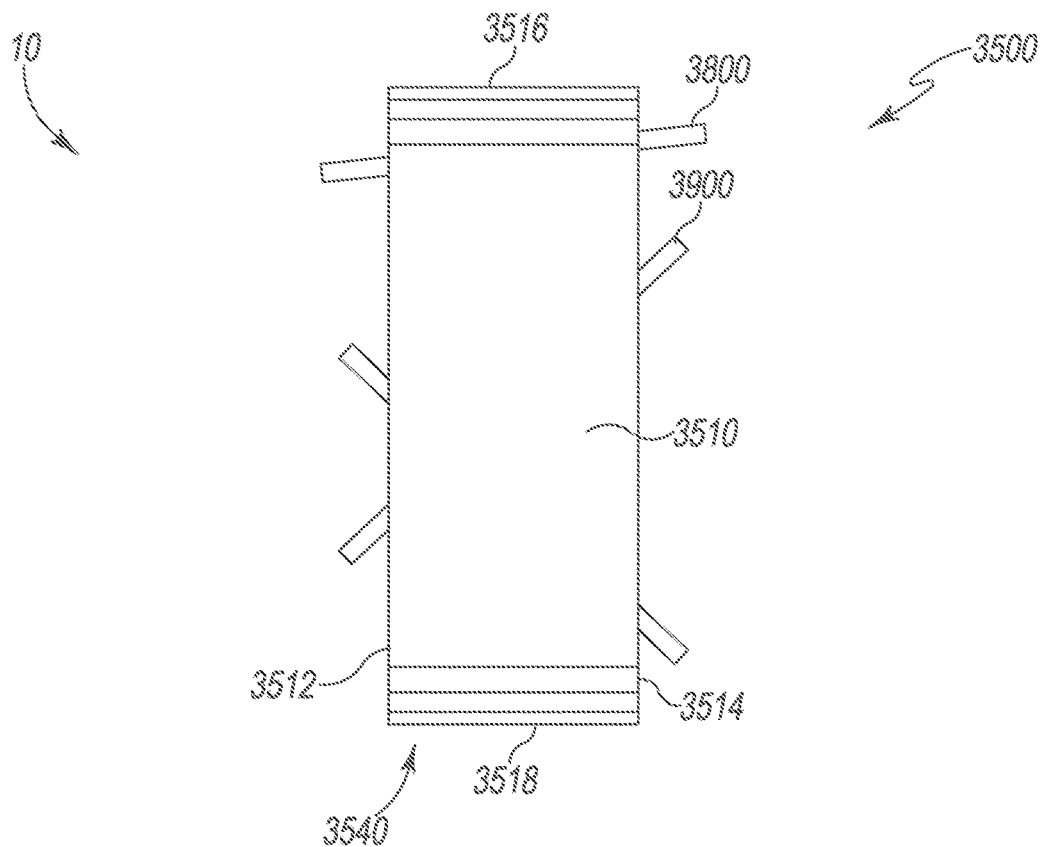
FIG. 39 is a side elevation view of the all-polymer 4-in-1 cutting block of FIG. 38.
Figure 40:
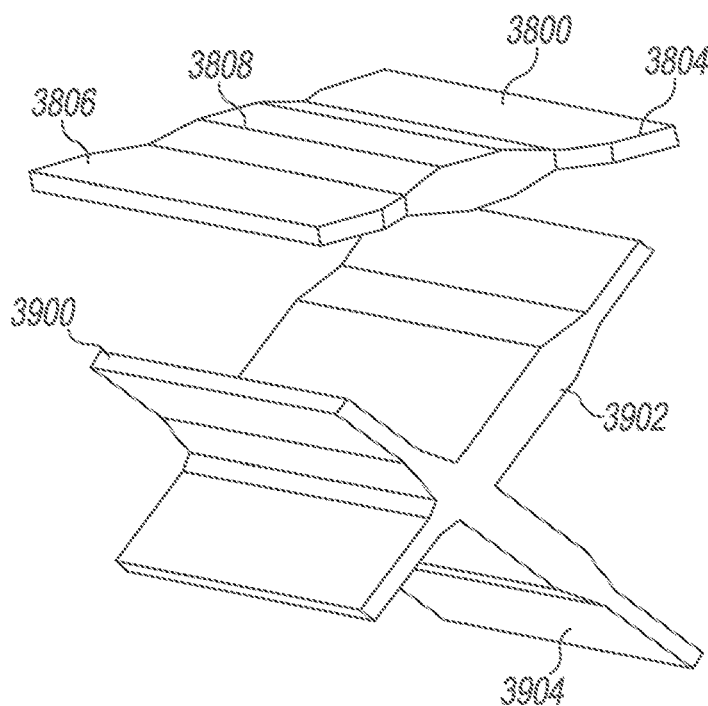
FIG. 40 is a perspective view of the sacrificial anterior cutting guide core and the sacrificial chamfer cutting guide core of FIG. 38.
Figure 41:
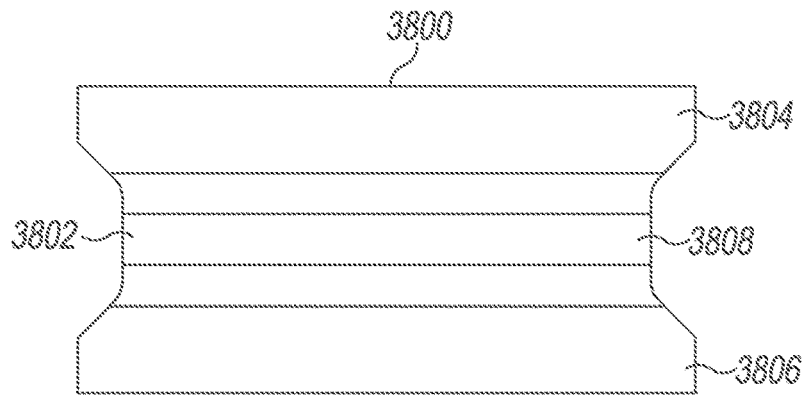
FIG. 41 is a top plan view of the sacrificial anterior cutting guide core of FIG. 40.

Referring now to FIG. 34, the above-described all-polymer 4-in-1 cutting block 2500 may be used in a method 3400 for performing an orthopaedic surgical procedure. The method 3400 begins with block 3402 in which the all-polymer 4-in-1 cutting block 2500 is assembled. To do so, in block 3404, the polymer chamfer cutting guide insert 2570 is attached to the polymer body 2510. As discussed above, the polymer chamfer cutting guide insert 2570 may be received in the chamfer cutting guide recess 2560 of the polymer body 2510. In doing so, the guide arms 2572, 2574 of the polymer chamfer cutting guide insert 2570 are received in the guide tracks 2582, 2584 of the polymer body in block 3406. In block 3408, the polymer chamfer cutting guide insert 2570 is secured to the polymer body 2510 via the securing devices 2590.

In block 3410, the assembled all-polymer 4-in-1 cutting block 2500 is secured to a surgically-prepared distal end of the patient's femur. For example, the all-polymer 4-in-1 cutting block 2500 may be secured to the patient's femur using bone screws and/or pins, similar to a typical 4-in-1 cutting block. In block 3412, an orthopaedic surgeon may perform a femoral resectioning procedure using the assembled all-polymer 4-in-1 cutting block 2500. For example, the orthopaedic surgeon may perform an anterior femoral cut using the polymer anterior cutting guide 2530, a posterior femoral cut using the polymer posterior cutting guide 2540, and a pair of chamfer cuts using the polymer chamfer cutting guide 2550.

Referring now to FIGS. 35-45, in another illustrative embodiment, the orthopaedic surgical instrument 10 is embodied as an all-polymer 4-in-1 cutting block 3500. The illustrative all-polymer 4-in-1 cutting block 23500 includes a polymer body 3510 having an outer surface 3512 and a bone-engaging surface 3514 opposite the outer surface 3512. The polymer body 3510 also includes an anterior end 3516 and a posterior end 3518 opposite the anterior end 3516, a medial side 2522, and a lateral side 2524 opposite the medial side 2522. Although not shown in the illustrative figures, the polymer body 3510 may also a number of mounting apertures defined therethrough and configured to facilitate the attachment of the all-polymer 4-in-1 cutting block 3500 to a distal end of the patient's surgically-prepared femur using corresponding securing devices, such as bone screws.

Figure 45:
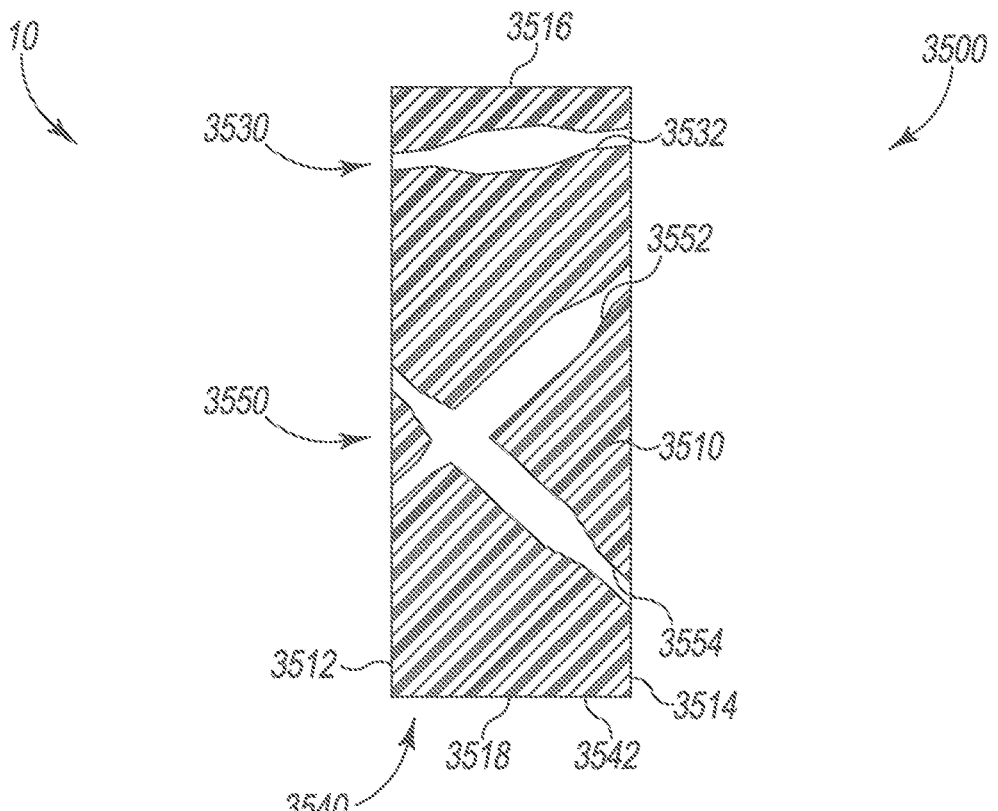
FIG. 45 is a cross-sectional is a cross-sectional view of the all-polymer 4-in-1 cutting block of FIG. 35 taken generally along line 45-45 of FIG. 35 with the sacrificial cutting guide cores removed from the polymer body of the all-polymer 4-in-1 cutting block.

The polymer body 3510 of the all-polymer 4-in-1 cutting block 3500 also includes a polymer anterior cutting guide 3530, a polymer posterior cutting guide 2540, and a polymer chamfer cutting guide 3550. As best shown in FIG. 45, the anterior cutting guide 3530 is embodied as a captured cutting slot 3532 that extends from the outer surface 3512 to the bone-engaging surface 3514 of the polymer body 3510. The polymer posterior cutting guide 3540 is embodied as a posterior cutting surface 3542 that also extends from the outer surface 3512 to the bone-engaging surface 3514 of the polymer body 3510. The polymer chamfer cutting guide 3550 is formed from a captured anteriorly-angled cutting slot 3552 and a captured posteriorly-angled cutting slot 3554, which intersect each other and extend from the outer surface 3512 to the bone-engaging surface 3514 of the polymer body 3510.

As shown in FIGS. 38-45 and described in more detail below, each of the polymer anterior cutting guide 3530 and the polymer chamfer cutting guide 3550 is formed during an injection molding process using a sacrificial anterior cutting guide core 3800 and a sacrificial chamfer cutting guide core 3900, respectively. The cutting guide cores 3800, 3900 are "sacrificial" in that they melted away from the polymer body 3510 after the polymer body 3510 has been formed via an injection molding process as described in more detail below. To facilitate such sacrificial removing, each of the cutting guide cores 3800, 3900 is formed from a metal material (e.g., a metal alloy) having a melting point that is lower than the polymer used to form the polymer body 3510. For example, in the illustrative embodiment, the cutting guide cores 3800, 3900 are formed from a metal material having a melting point of 550 degrees Fahrenheit or less, such as a tin bismuth alloy.

Figure 42:
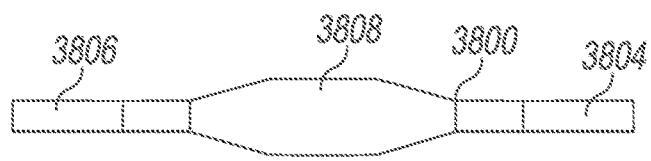
FIG. 42 is a side elevation view of the sacrificial anterior cutting guide core of FIG. 40.

As shown in FIGS. 39-45, the sacrificial anterior cutting guide core 3800 is used during the injection molding process to define the captured cutting slot 3532, which defines the polymer anterior cutting guide 3530. The anterior cutting guide core 3800 includes an elongated body 3802 having a first end 3804, a second end 3806 opposite the first end 3804, and a cutting guide molding section 3808 defined between the first end 3804 and the second end 3806. As best shown in FIG. 42, the cutting guide molding section 3808 has a thickness that is greater than the thickness of the first end 3804 and the second end 3806.

Figure 43:
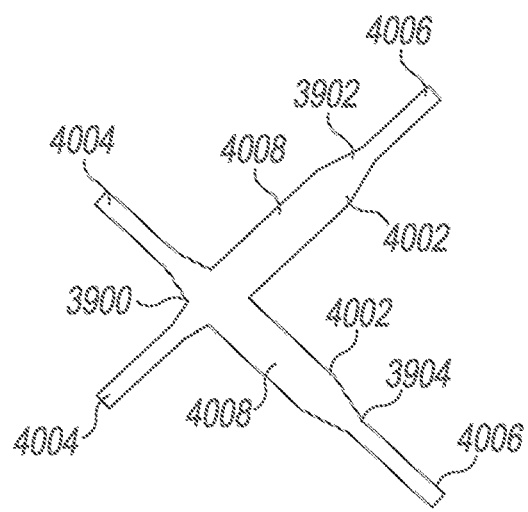
FIG. 43 is a side elevation view of the sacrificial chamfer cutting guide core of FIG. 40.
Figure 44:
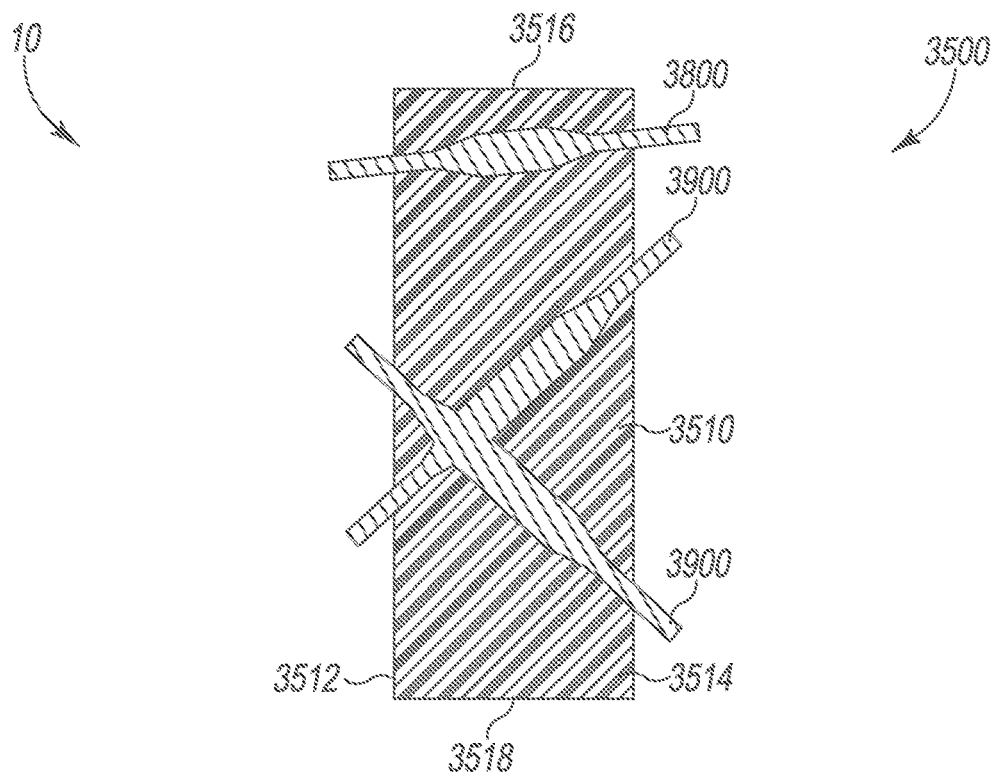
FIG. 44 is a cross-sectional is a cross-sectional view of the all-polymer 4-in-1 cutting block of FIG. 35 taken generally along line 44-44 of FIG. 38 with the sacrificial cutting guide cores inserted into the polymer body of the all-polymer 4-in-1 cutting block.

Similar to the sacrificial anterior cutting guide core 3800, the sacrificial chamfer cutting guide core 3900 is used during the injection molding process to define the captured anteriorly-angled cutting slot 3552 and the captured posteriorly-angled cutting slot 3554, which cooperate to define the polymer chamfer cutting guide 3550. The illustrative sacrificial chamfer cutting guide core 3900 includes an anteriorly-angled cutting guide core 3902 and a posteriorly angled cutting guide core 3904, which extend through each other as best shown in FIG. 43. The anteriorly-angled cutting guide core 3902 and the posteriorly angled cutting guide core 3904 extend away from each other at an oblique angle. Each of the anteriorly-angled cutting guide core 3902 and the posteriorly angled cutting guide core 3904 includes an elongated body 4002 having a first end 4004, a second end 4006 opposite the first end 4004, and a cutting guide molding section 4008 defined between the first end 4004 and the second end 4006. As best shown in FIG. 44, each cutting guide molding section 4008 has a thickness that is greater than the thickness of the corresponding first end 4004 and the second end 4006.

Figure 46:
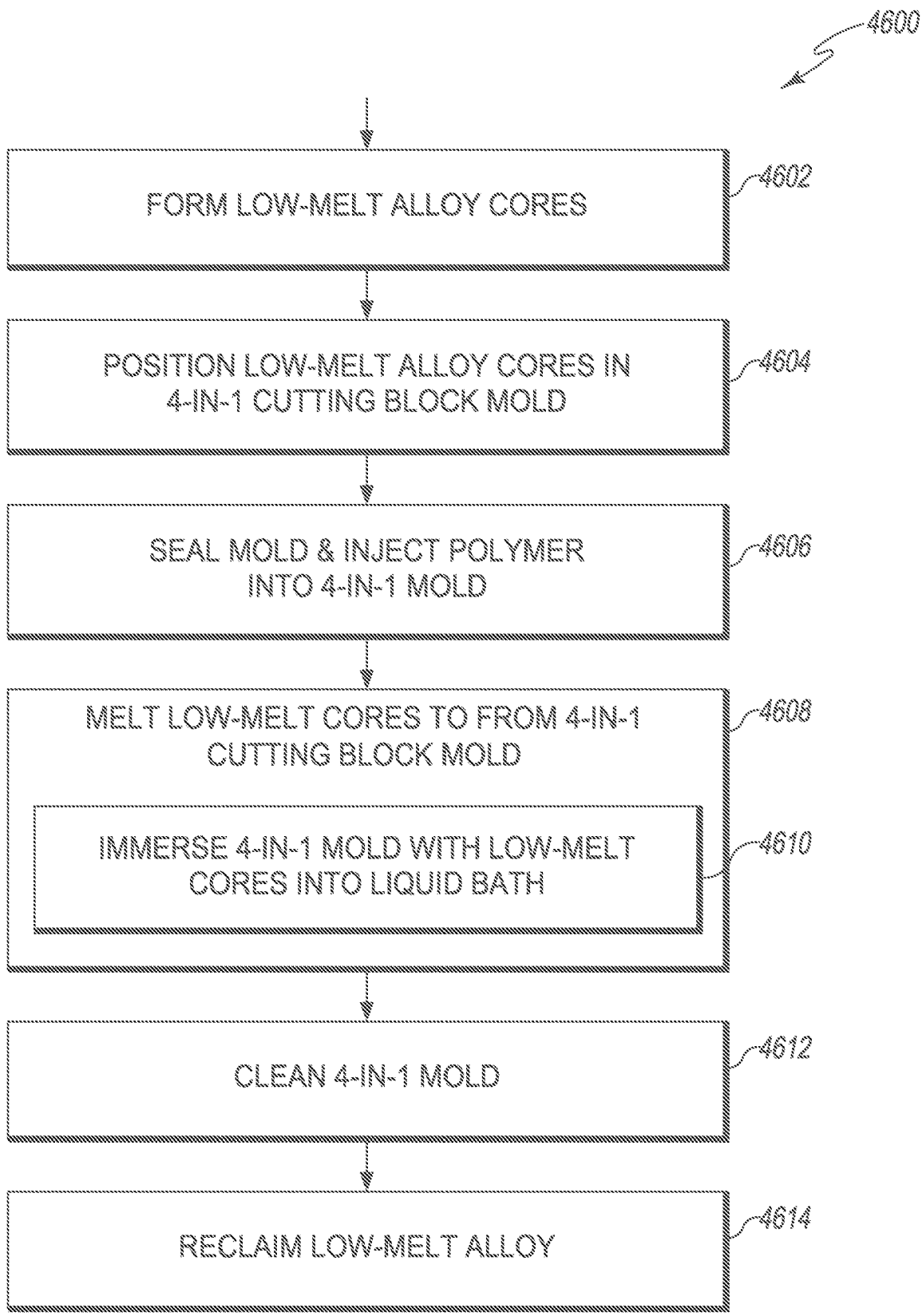
FIG. 46 is a simplified flow diagram of a method for fabricating the all-polymer 4-in-1 cutting block of FIG. 35.

Referring now to FIG. 46, a method 4600 for fabricating the all-polymer 4-in-1 cutting block 3500 is shown. The method 4600 begins with block 4602 in which the sacrificial anterior cutting guide core 3800 and the sacrificial chamfer cutting guide core 3900 are formed or otherwise obtained. As discussed above, each of the cutting guide cores 3800, 3900 is formed from a metal alloy or material having a relatively low melting point (i.e., a melting point that is less than the melting point of the polymer used to form the all-polymer 4-in-1 cutting block 3500).

In block 4604, the cutting guide cores 3800, 3900 are positioned in an injection mold of the all-polymer 4-in-1 cutting block 3500. The injection mold is subsequently sealed and injected with a polymer in block 4606 to form the all-polymer 4-in-1 cutting block 3500.

After the all-polymer 4-in-1 cutting block 3500 has been formed in block 4606, the method 4600 advances to block 4608 in which the cutting guide cores 3800, 3900 are removed from the all-polymer 4-in-1 cutting block 3500. To do so, in the illustrative embodiment, the cutting guide cores 3800, 3900 are melted away from the all-polymer 4-in-1 cutting block 3500. For example, in block 4610, the all-polymer 4-in-1 cutting block 3500 with the cutting guide cores 3800, 3900 installed therein may be immersed in a liquid bath having a temperature greater than the melting temperature of the cutting guide cores 3800, 3900, which causes the cutting guide cores 3800, 3900 to melt away from the all-polymer 4-in-1 cutting block 3500.

In block 4612, the resulting all-polymer 4-in-1 cutting block 3500 may be cleaned. The cleaning process may remove any extraneous polymer pieces from the all-polymer 4-in-1 cutting block 3500. Subsequently, in block 4614, the melted metal or metal alloy may be reclaimed from the liquid bath and reused in a subsequent polymer cutting block fabrication process.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A polymer 4-in-1 cutting block for performing an orthopedic surgical procedure on a distal end of a patient's femur, the polymer 4-in-1 cutting block comprising:
   a first polymer half-block having a plurality of first cutting slots and a plurality of alignment receptacles formed in an inner sidewall of the first polymer half-block;
   a second polymer half-block separate from the first polymer half-block and configured to be coupled to the first polymer half-block to form an assembled polymer 4-in-1 cutting block, the second polymer half-block having a plurality of second cutting slots and a plurality of alignment protrusions formed in an inner sidewall of the second polymer half-block,
   wherein, when the second polymer half-block is coupled to the first polymer half-block, (i) each first cutting slot cooperates with a corresponding second cutting slot to define a respective polymer cutting guide and (ii) each alignment protrusion is received in a corresponding alignment receptacle.

2. The polymer 4-in-1 cutting block of claim 1, wherein the inner sidewall of the first polymer half-block confronts the inner sidewall of the second polymer half-block when the second polymer half-block is coupled to the first polymer half-block.

3. The polymer 4-in-1 cutting block of claim 1, wherein, when the second polymer half-block is coupled to the first polymer half-block, the plurality of first cutting slots and the plurality of second cutting slots cooperate to define an anterior polymer cutting guide and two polymer chamfer cutting guides.

4. The polymer 4-in-1 cutting block of claim 1, wherein each respective polymer cutting guide is devoid of any metal inserts.

5. The polymer 4-in-1 cutting block of claim 1, wherein an anterior edge of the inner sidewall of the first polymer half-block and an anterior edge of the inner sidewall of the second polymer half-block are both chamfered inwardly.

6. The polymer 4-in-1 cutting block of claim 1, wherein the plurality of alignment receptacles formed in the inner sidewall of the first polymer half-block comprises a plurality of complex-shaped alignment receptacles and the plurality of alignment protrusions formed in the inner sidewall of the second polymer half-block comprises a plurality of complex-shaped alignment receptacles,
wherein no two complex-shaped alignment receptacles have an identical shape and wherein no two complex-shaped alignment protrusions have an identical shape.

7. The polymer 4-in-1 cutting block of claim 6, wherein the plurality of complex-shaped alignment receptacles comprises at least three complex-shaped alignment receptacles and wherein the plurality of complex-shaped alignment protrusions comprises at least three complex-shaped alignment protrusions.

8. The polymer 4-in-1 cutting block of claim 6, wherein the plurality of alignment receptacles formed in the inner sidewall of the first polymer half-block further comprises at least one cylindrical-shaped alignment receptacle and wherein the plurality of alignment protrusions comprises a least one cylindrical-shaped alignment protrusion.

9. The polymer 4-in-1 cutting block of claim 1, wherein each alignment receptacles of the plurality of alignment receptacles include an inner lip configured to abut an outer edge of a corresponding one of the plurality of alignment protrusions when the second polymer half-block is coupled to the first polymer half-block.

10. The polymer 4-in-1 cutting block of claim 1, further comprising a plurality of metallic securing devices configured to secure the second polymer half-block to the first polymer half-block.

11. A polymer 4-in-1 cutting block for performing an orthopedic surgical procedure on a distal end of a patient's femur, the polymer 4-in-1 cutting block comprising:
a first polymer half-block having a plurality of first cutting slots and a plurality of alignment receptacles formed in an inner sidewall of the first polymer half-block;
a second polymer half-block separate from the first polymer half-block and coupled to the first polymer half-block to form an assembled polymer 4-in-1 cutting block, the second polymer half-block having a plurality of second cutting slots and a plurality of alignment protrusions formed in an inner sidewall of the second polymer half-block, wherein each alignment protrusion of the plurality of alignment protrusion is received in a corresponding alignment receptacle of the plurality of alignment receptacles of the first polymer half-block; and
a plurality of securing devices extending through each of the first polymer half-block and securing the first and second polymer half-blocks to each other,
wherein each first cutting slot cooperates with a corresponding second cutting slot to define a respective polymer cutting guide.

12. The polymer 4-in-1 cutting block of claim 11, wherein the inner sidewall of the first polymer half-block confronts the inner sidewall of the second polymer half-block.

13. The polymer 4-in-1 cutting block of claim 11, wherein the plurality of first cutting slots and the plurality of second cutting slots cooperate to define an anterior polymer cutting guide and two polymer chamfer cutting guides.

14. The polymer 4-in-1 cutting block of claim 11, wherein each respective polymer cutting guide is devoid of any metal inserts.

15. The polymer 4-in-1 cutting block of claim 11, wherein an anterior edge of the inner sidewall of the first polymer half-block and an anterior edge of the inner sidewall of the second polymer half-block are both chamfered inwardly.

\* \* \* \* \*